United States Patent [19]

Sunkel et al.

[11] Patent Number: 4,727,066
[45] Date of Patent: Feb. 23, 1988

[54] ESTERS OF 1,4-DIHYDROPYRIDINES AND MEDICAMENTS CONTAINING THE SAME

[75] Inventors: Carlos E. Sunkel; Miguel Fau de Casa-Juana, both of Madrid, Spain; Peter R. Statkow, Geneva; Danielle Straumann, Martigny, both of Switzerland

[73] Assignee: Cermol S.A., Geneva, Switzerland

[21] Appl. No.: 880,148

[22] Filed: Jun. 30, 1986

Related U.S. Application Data

[62] Division of Ser. No. 637,216, Jul. 20, 1984, Pat. No. 4,656,181.

[30] Foreign Application Priority Data

Nov. 24, 1982 [CH] Switzerland .................. 6858/82

[51] Int. Cl.⁴ .................. C07D 401/12; C07D 405/14; A61K 31/625; A61K 31/455
[52] U.S. Cl. .................. 514/161; 514/252; 514/332; 514/356; 544/364; 544/365; 546/263; 546/321
[58] Field of Search .............. 546/321, 193, 194, 256, 546/263; 544/364, 365; 514/252, 332, 318, 333, 356, 161

[56] References Cited

U.S. PATENT DOCUMENTS

3,996,234 12/1976 Bossert et al. .................. 546/321
4,532,248 7/1985 Franckowick et al. ............ 514/302
4,618,607 10/1986 Araki et al. .................. 544/365

OTHER PUBLICATIONS

Bossert et al., Angew. Chem. Int. Ed. Engl. 20, pp. 762-769 (1981).

*Primary Examiner*—Henry R. Jiles
*Assistant Examiner*—Dale A. Bjorkman
*Attorney, Agent, or Firm*—Stevens, Davis, Miller & Mosher

[57] ABSTRACT

The preparation of esters of 1,4-dihydropyridine, useful in the prevention and treatment of cardiovascular disorders such as atheroma, of the formula

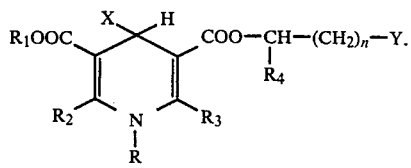

wherein X is a phenyl moiety and Y is piperazine, piperidine or an amide of a benzenecarboxylic acid, is described.

5 Claims, No Drawings

ESTERS OF 1,4-DIHYDROPYRIDINES AND MEDICAMENTS CONTAINING THE SAME

This is a division of application Ser. No. 637,216, filed July 20, 1984, now U.S. Pat. No. 4,656,181.

The present invention relates to new 1,4-dihydropyridines, to processes for their preparation and to medicaments containing the same, such medicaments being preferably used for their action on the blood vessels, and in particular as agents against coronary diseases or as anti-atheromatic agents. The applicant has discovered the important influence that have on the coronary vessels the new esters of 1,4-dihydropyridines (I) and their salts of the general formula:

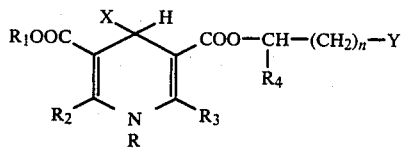
(I)

in which:
- R stands for a hydrogen atom, for a saturated or an unsaturated hydrocarbon radical or an alkylmorpholinic group,
- $R_2$ and $R_3$, which can be identical or different stand for a hydrogen atom, an alkyl group or an alkoxyalkyl group,
- $R_4$ stands for a hydrogen atom or a straight alkyl chain,
- n is a number equaling 0, 1, 2 or 3,
- X stands for an aryl radical which can have one to three substituents nitro, cyano, azido, alkyl, alkoxy, hydroxy, acyloxy, carbaloxy, amino, acylamino, alkylamino, $S(O)_m$-alkyl where m equals 0, 1 or 2, phenyl, trifluoromethyl or halo, with these substituents being identical or different, a benzyl, styryl, cycloalkyl, cycxloalkenyl group, or a naphthyl, quinolyl, isoquinolyl, pyridyl, pyrimidyl, diphenyl, furyl, pyrryl or thiophenyl radical which can be substituted by an alkyl, alkoxy, dialkylamino, nitro or halo group,
- $R_1$ is a hydrocarbon radical which can be straight or branched, saturated, unsaturated or cyclic; it can also be interrupted by one or two atoms of oxygen or sulfur and can be substituted by one or two hydroxyl groups; $R_1$ can also designate the

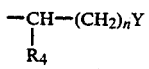

group; the two substituents Y can be identical or different and have the following structures:
Y designates N-substituted amides of nicotinic, salicylic and 4-hydroxybenzoic acids or N-substituted piperazines of the following formula

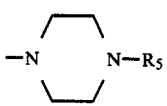

where $R_5$ is an alkyl, acyl, or an arylsulfonyl radical. Y can also designate another group of products having for formula $-OOC-R_6$ and $-O-R_6$, where $R_6$ is a hydrocarbon radical which can be saturated or cyclic, branched or not, heterocyclic or aromatic, and which can be substituted with one or two nitro, halo, hydroxy, acetyl, alkoxy, trifluoromethyl or acylamino groups. Y can also designate a 2-tetrahydrofuryl or a N-(4-benzoyl-piperidinyl) group.

These products (I) can be prepared by using the following processes:

(a) By reacting esters of β-ketocarboxylic acids of the formula (II)

$$R_2-CO-CH_2-COOR_1 \quad (II)$$

(where $R_1$ and $R_2$ are defined as above) with amines of the formula (III)

$$R-NH_2 \quad (III)$$

for obtaining enamines of the following formula (IV)

(IV)

(where R, $R_1$ and $R_2$ are defined as above) which are eventually isolated and thereafter reacted with an ylidenic derivative of the formula (V)

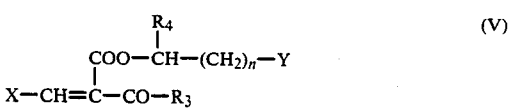
(V)

(where X, $R_3$, $R_4$, n an Y are defined as above) which are obtained by reacting aldehydes of the formula (VI)

$$X-CHO \quad (VI)$$

(where X is defined as above) with esters of β-ketocarboxylic acids of the formula (VII):

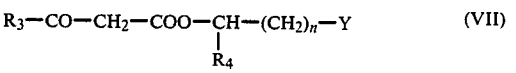
(VII)

(where $R_3$, $R_4$, n and Y are defined as above); or (b) By reacting β-ketocarboxylic acids of the formula (VII) with amines of the formula (III) for obtaining enamines of the formula

(VIII)

(where R, $R_3$, $R_4$, n and Y are defined as above) which are eventually isolated and thereafter reacted with ylidenic derivatives of the formula (IX)

$$\underset{X-CH=C-CO-R_2}{\overset{COOR_1}{|}} \quad (IX)$$

(where X, $R_1$ and $R_2$ are defined as above) which are obtained by reacting aldehydes of the formula (VI) with esters of β-ketocarboxylic acids of the formula (II); or (c) By reacting esters of β-ketocarboxylic acids of the formula (II) with enamines of the formula (VIII) and aldehydes of the formula (VI); or (d) By reacting esters of β-ketocarboxylic acids of the formula (VII) with enamines of the formula (IV) and aldehydes of the formula (VI); or (e) By reacting two moles of β-ketocarboxylic acids of the formula (VII) with one mole of amine of the formula (III) and one mole of aldehyde of the formula (VI); or (f) In certain cases, where Y designates a group with a substituted atom of oxygen or nitrogen, the compound (I) can also be obtained by reacting the 1,4-dihydropyridine of the formula (X)

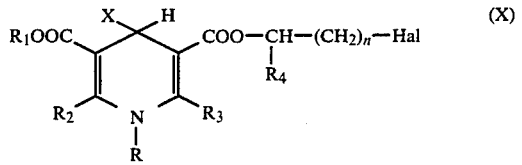

(where X, R, $R_1$, $R_2$ $R_3$, $R_4$ and n are defined as above and Hal stands for a halogen atom) with a compound of the formula (XI)

HY        (XI)

(where Y is defined as above and H is capable of a substitution reaction). When desired, salts of the products prepared according to the processes (a) to (f) can be prepared by using an acid. In formula (I), the saturated or unsaturated hydrocarbon radical R is preferably a straight or a branched $C_1$ to $C_4$ alkyl such as methyl, ethyl, n-propyl, isopropyl, n-butyl and tert-butyl, or a straight or a branched $C_2$ to $C_4$ alkenyl such as ethenyl, 1-propenyl, 2-propenyl and butenyl. R can also be an alkylmorpholinic radical such as ethylmorpholinyl and propylmorpholinyl.

In the formula (I), the saturated or unsaturated hydrocarbon $R_1$ is preferably a straight or a branched $C_1$ to $C_4$ alkyl, such as methyl, ethyl, n-propyl, isopropyl, n-butyl, isobutyl and tert-butyl or a straight or a branched $C_2$ to $C_4$ alkenyl such as ethenyl, 1- or 2-propenyl, and butenyl. $R_1$ can also be a cycloalkyl with preferably 5 or 6 atoms of carbon, such as cyclopentyl, cyclohexyl, and 3,3,5-trimethylcyclohexyl. When an oxygen or a sulfur is included in the hydrocarbon chain, $R_1$ can be represented by the radicals —W—O—Z and —W—S—Z, where W designates a straight or a branched $C_1$ to $C_3$ alkylene, such as methylene, ethylene and isopropylene, an Z designates a straight or a branched $C_1$ to $C_4$ alkyl radical such as methyl, ethyl, n-propyl, isopropyl, n-butyl and tert-butyl. $R_1$ can also be the cyclic 2-tetrahydrofurfurylic radical.

In the formula (I), the $R_2$ and $R_3$ alkyl groups are preferably straight or branched $C_1$ to $C_4$ alkyls, such as methyl, ethyl, n-propyl, isopropyl, and tert-butyl. The $R_2$ and $R_3$ alkoxyalkyl groups are preferably —W—O—Z radicals with W an Z defined as above.

In the formula (I), the $R_4$ alkyl group is preferably a straight $C_1$ to $C_2$ alkyl (methyl or ethyl).

In the formula (I), the aryl group X (which can be substituted) is an aryl with preferably 6 to 10 carbons, and in particular 6 carbons in the aryl portion. Phenyl or naphthyl groups (with possible substituents) can be given as examples of such aryl groups. The aryl X can have one or several—preferably 1 to 3 and in particular 1 or 2—substituents, which can be identical or different. These substituents can for example be phenyl or alkyl groups such as methyl, ethyl, n-propyl, isopropyl, n-butyl, isobutyl and tert-butyl; they can also be alkoxy groups such as methoxy, ethoxy, propyloxy and isopropyloxy; trifluoromethyl; hydroxy; halo, preferably fluoro, chloro, bromo and iodo; cyano, nitro, azido, amino, monoalkyl or dialkylamino with preferably 1 to 4 and in particular 1 or 2 carbons in the alkyl group such as for example methylamino, methylethylamino, isopropylamino and diethylamino; carbalkoxy such as carbmethoxy and carbethoxy; acylamino group such as acetylamino and propionylamino; acyloxy group such as acetyloxy and propionyloxy; $S(O)_m$-alkyl group where m equals 0, 1 or 2 and the alkyl group has preferably 1 to 4 carbons and in particular 1 to 2 carbons, such as methylthio, ethylthio, methylsulfoxyl, ethylsulfoxyl, methylsulfonyl and ethylsulfonyl. The alkyl and alkoxy groups present as substituents on the naphtyl, quinolyl, isoquinolyl, pyridyl, pyrimidyl, diphenyl, furyl or pyrryl group X are alkyl or alkoxy radicals with a straight or a branched chain such as methyl, ethyl, n-propyl, isopropyl, n-butyl, tert-butyl, as well as methoxy, ethoxy, n-propoxy, isopropoxy, and tert-butoxy. The halogen present as a substituent on the X groups given above is fluorine, chlorine, bromine or iodine. The dialkylamino group also present as substituent on the X groups contains preferably 1 to 4 and in particular 1 or 2 carbons in the alkyl groups. The following examples of alkyl groups can be given: methyl, ethyl, n-propyl, isopropyl, n-butyl, isobutyl and tert-butyl.

In the formula (I), the group Y stands preferably for N-substituted amides of nicotinic, salicylic and 4-hydroxybenzoic acids and for monoalkylated, monoacylated and sulfonylated piperazines of the following formula

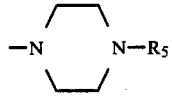

where $R_5$ is a straight or branched, saturated or unsaturated alkyl such as methyl, ethyl, isopropyl, benzyl, vinyl and cinnamyl. $R_5$ also stands for acyl radicals, such as acetyl, 2-furoyl, 2-thiophenecarbonyl and cinnamoyl. $R_5$ further stands for arylsulfonyl radicals such as benzenesulfonyl; these aromatic radicals can in turn be substituted by one or several alkyl groups such as methyl, ethyl and trifluoromethyl, alkoxy such as methoxy or ethoxy, acetylamine, one or several halogens such as chlorine, fluorine bromine and iodine. Y further stands for —OOC—$R_6$ and —O—$R_6$ groups, where $R_6$ stands for a saturated or an unsaturated hydrocarbon, preferably for a straight or a branched alkyl with 1 to 4 carbons, and in particular with 1 to 3 carbons such as methyl, ethyl and isopropyl; a cyclic hydrocarbon group such as cyclohexyl; an alkenyl group such as ethenyl or 2-propenyl; a heterocyclic group such as furyl, thiophényl and pyridyl; an aromatic group such as phenyl. The following examples of substituents which can be present on this phenyl group can be given: nitro, halo (for example chloro and bromo), alkoxy (methoxy, ethoxy), hydroxy, acetyl, trifluoromethyl and acylamino (acetylamino).

The salts of the compounds of formula (I) are all salts resulting from the addition of acids which are nontoxic and physiologically acceptable. The following examples of inorganic and organic acids which form salts with the compounds of formula (I) can be given: halohydric acids such as hydrochloric acid and hydrobromic acid, phosphonic acids, sulfuric acid, nitric acid, monocarboxylic acids, dicarboxylic acids, hydroxycarboxylic acids such as citric acid, malic acid, succinic acid, fumaric acid, tartaric acid, citric acid, salicylic acid, lactic acid, 1,5-naphthalenecarboxylic acid, methanesulfonic acid and toluenesulfonic acid.

The conditions in which the reactions (a) to (f) are performed are the following:

Is considered as a diluent water and all the inert organic solvents. These are preferably alcohols such as methanol, ethanol, isopropanol and n-butanol; ethers, for example lower dialkyl ethers such as diethyl ether or cyclic ethers such as tetrahydrofuran and dioxane; lower aliphatic carboxylic acids such as acetic acid and propionic acid; lower dialkyl formamides such as dimethylformamide; lower alkylnitriles such as acetonitrile; dimethylsulfoxyde, liquid heteroaromatic bases such as pyridine; mixtures of such diluents, including water. The reaction can also be carried out without using a diluent.

The reaction temperatures can vary from approximately 20° C. to 150° C., and preferably between 50° C. and 100° C. The reaction can in particular be carried out at the boiling temperature of the diluent. The reaction can be carried out at atmospheric pressure, but higher pressures can also be used. The reactants are preferably used in approximately a molar ratio. Ammonia in preferably used in excess, e.g. of one to two moles. The molar ratio can vary within large limits without affecting the results.

The reaction time varies between 45 minutes and 10 hours.

The product obtained according to the process of the invention is separated and isolated according to known practices, such as recrystallisation in an appropriate solvent or a mixture of appropriate solvents.

The characterization of the structures of the different compounds (I) was carried out using quantitative elemental analysis and IR and NMR analyses.

Further to the products described in the Examples, the new active substances include the following:

2-(4-acetylaminophenoxy)ethyl 2,6-dimethyl-5-methoxycarbonyl-4-(3-pyridyl)1,4-dihydropyridine-3-carboxylate, 2-(4-acetylaminophenoxy)ethyl 2,6-dimethyl-5-ethoxycarbonyl-4-(3-trifluoromethylphenyl)-1,4-dihydropyridine-3-carboxylate, 2-(4-acetylaminophenoxy)ethyl 4-(2,3-dichlorophenyl)-2,6-diethyl-5-(-tetrahydrofurfuryloxycarbonyl)-1,4-dihydropyridine-3-carboxylate, bis-2-(N-nicotinoylamino)ethyl 2,6-dimethyl-4-(2-nitrophenyl)-1,4-dihydropyridine-3,5-dicarboxylate, 2-(N-nicotinoylamino)ethyl 2,6-dimethyl-5-methoxycarbonyl-4-(3-pyridyl)-1,4-dihydropyridine-3-carboxylate, 2-(N-nicotinoylamino)ethyl 2,6-dimethyl-5-(2-methoxyethoxycarbonyl)-4-(3-trifluoromethylphenyl)-1,4-dihydropyridine-3-carboxylate, 2-(N-nicotinoylamino)ethyl 4-(2,3-dichlorophenyl)-2,6-dimethyl-5-(2-methylthioethoxycarbonyl-1,4-dihydropyridine-3-carboxylate, 2-(N-salicylamido)ethyl 2,6-dimethyl-5-methoxycarbonyl-4-(3-pyridyl)-1,4-dihydropyridine-3-carboxylate, 2-(N-salicylamido)ethyl 4-(2,3-dichlorophenyl)-2,6-dimethyl-5-ethoxycarbonyl-1,4-dihydropyridine-3-carboxylate, 2-(4-(2-furoyl)-1-piperazinyl))ethyl 2,6-dimethyl-5-methoxycarbonyl-4-(2-pyridyl)-1,4-dihydropyridine-3-carboxylate, 2-(4-(2-furoyl)-1-piperazinyl)ethyl 2,6-dimethyl-5-ethoxycarbonyl-4-(3-trifluoromethylphenyl)-1,4-dihydropyridine-3-carboxylate, 2-(4-(2-furoyl)-1-piperazinyl)ethyl 4-(2,3-dichlorophenyl)-2,6-dimethyl-5-isopropoxycarbonyl-1,4-dihydropyridine-3-carboxylate, 2-(N-salicylamide)ethyl 4-(2,3-dichlorophenyl)-2,6-dimethyl-1-(2-(N-morpholine)ethyl)-5-(2-methoxyethoxycarbonyl)-3-carboxylate, 2-(4-cinnamoyl-1-piperazinyl)ethyl 2,6-dimethyl-5-ethoxycarbonyl-4-(3-trifluoromethylphenyl)-1,4-dihydropyridine-3-carboxylate, 2-(4-(4-methoxy)cinnamoyl-1-piperazinyl)ethyl 2,6-dimethyl-5-methoxycarbonyl-4-(3-pyridyl)-1,4-dihydropyridine-3-carboxylate, 2-(4-cinnamoyl-1-piperazinyl)ethyl 4-(2,3-dichlorophenyl)-2,6-dimethyl-5-(2-methylthioethoxycarbonyl)-1,4-dihydropyridine-3-carboxylate.

As was indicated previously, the applicant has found that the compounds of the invention can be advantageously used as pharmacologically active substances in medicaments used for the treatment of various diseases. As examples of such diseases, one can mention diseases of the coronary vessels, for which these compounds are particularly effective. The applicant has found that the compounds of the invention generally have anti-atheromatic properties, and can therefore exert a protective effect against necrosis.

In experiments carried out on animals, it was found that when administered at the same therapeutical level, the new compounds were more active and less toxic than similar known therateutical agents.

To achieve the desired therapeutic effects, the new products can be administered orally under an appropriate form. The doses which are then used can vary between 5 and 500 mg of active ingredient which can be combined, when desired, with an inert excipient or an additional active ingredient.

These doses can be used in preventive or curative treatments.

EXAMPLE 1

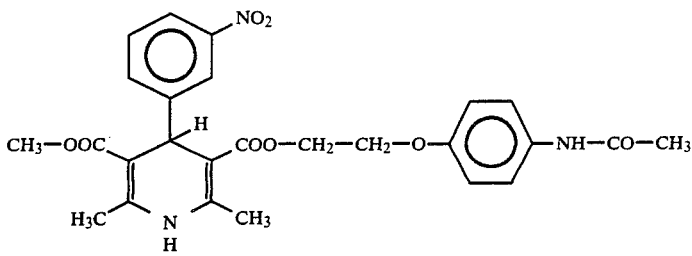

15 g (0.04 moles) of 2-(4-acetylaminophenoxy)-ethyl 2-(3-nitrobenzilidene)acetylacetate and 4.19 g (0.04 moles) of methyl 3-aminocrotonate are heated for 4 hours under reflux in 40 ml of ethanol. The solution is cooled to 7° C. to obtain 2-(4-acetylaminophenoxy)ethyl 2,6-dimethyl-5-methoxycarbonyl-4-(3-nitrophenyl)-1,4-dihydropyridine-3-carboxylate as yellow crystals melting—after recrystallisation in isopropanol—at 202°-204° C. The yield was 68% of the theoretical yield.

| Analysis for $C_{26}H_{27}N_3O_8$: | | | |
|---|---|---|---|
| | % C | % H | % N |
| Calculated | 61.29 | 5.35 | 8.25 |
| Found | 60.93 | 5.52 | 8.23 |

IR spectrum (KBr): $\nu(cm^{-1})$: 3360, 3210, 3080, 1700, 1670, 1510, 1350, 1240, 1210, 1090, 840, 780, 700.

NMR spectrum ($\delta$, $CDCl_3 + DMSO-d_6$): p.p.m: 9.4(1H, s); 8.6 (1H, s); 8–6.6 (8H, m); 5(1H, s); 4.4–4 (4H, m); 3.6 (3H, s) 2.3 (6H, s); 2(3H, s).

EXAMPLE 2

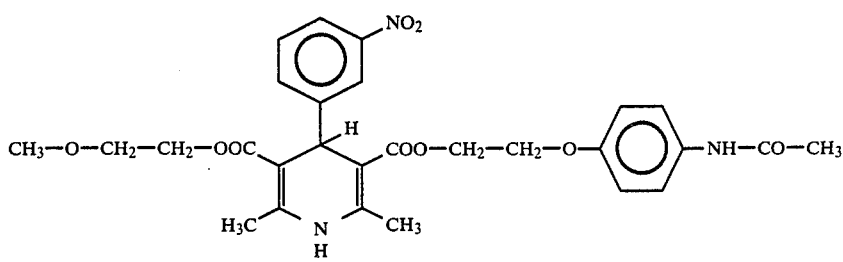

8.3 g (0.02 moles) of 2-(4-acetylaminophenoxy)ethyl 2-(3-nitrobenzylidene)acetylacetate and 3.2 g (0.02 moles) of 2-methoxyethyl 3-aminocrotonate are heated for 8 hours under reflux in 25 ml of ethanol. The solution is cooled to −5° C. to obtain 2-(4-acetylaminophenyl)ethyl 2,6-dimethyl-5-(2-methoxyethoxycarbonyl)-4-(3-nitrophenyl-1,4-dihydropyridine-3-carboxylate as a yellow powder melting—after recrystallisation in ethanol—at 95°-98° C. The yield is 64% of the theoretical yield.

| Analysis for $C_{26}H_{31}N_3O_9$: | | | |
|---|---|---|---|
| | % C | % H | % N |
| Calculated | 60.75 | 5.64 | 7.59 |
| Found | 60.55 | 5.79 | 7.42 |

IR spectrum (KBr): $\nu(cm^{-1})$: 3170, 1710, 1700, 1540, 1520, 1360, 1220, 1120, 1100, 870, 710.

NMR spectrum ($\delta$, $CDCl_3$): p.p.m: 8.2–6.6 (10H, m); 5.2 (1H, s); 4.4–4 (6H, m); 3.6–3.4 (2H, m); 3.3 (3H, s); 2.3 (6H, s); 2.1 (3H, s).

EXAMPLE 3

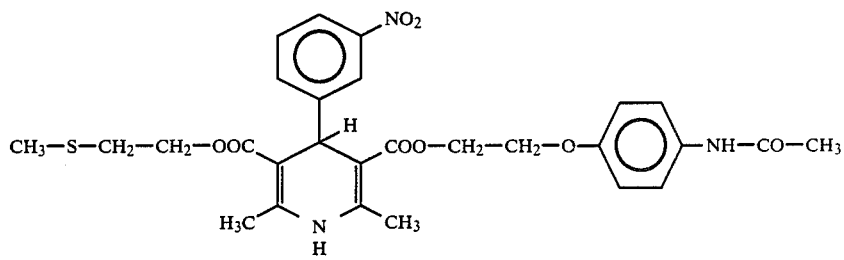

15 g (0.04 moles) of 2-(4-acetylaminophenoxy)ethyl 2-(3-nitrobenzylidene)acetylacetate and 6.37 g (0.04 moles) of 2-methylthioethyl 3-aminocrotonate are heated under reflux in 30 ml of ethanol during 8 hours. The solution is then cooled to −5° C. to obtain 2-(4-acetylaminophenoxy)ethyl 2,6-dimethyl-5-(2-methylthioethoxycarbonyl)-4-(3-nitrophenyl)-1,4-dihydropyridine-3-carboxylate as yellow crystals melting—after recrystallisation in ethanol—at 76° C.-80° C. The yield is 80% of the theoretical yield.

| Analysis for $C_{28}H_{31}N_3O_8S$: | | | | |
|---|---|---|---|---|
| | % C | % H | % N | % S |
| Calculated | 59.04 | 5.49 | 7.38 | 5.63 |

| Analysis for C₂₈H₃₁N₃O₈S: | | | | |
|---|---|---|---|---|
| | % C | % H | % N | % S |
| Found | 59.92 | 5.41 | 7.55 | 5.81 |

IR spectrum (KBr): ν(cm⁻¹): 3300, 3200, 1680, 1540, 1520, 1220, 1130, 1030, 840, 720.

NMR spectrum (δ, CDCl₃+DMSO-d₆): p.p.m: 9.2 (1H, s); 8.2 (1H, s); 7.6–6.6 (8H, m); 5.7 (1H, s); 4.2 (4H, m); 3.5 (3H, s); 2.3 (6H, d); 2.1 (3H, s).

EXAMPLE 5

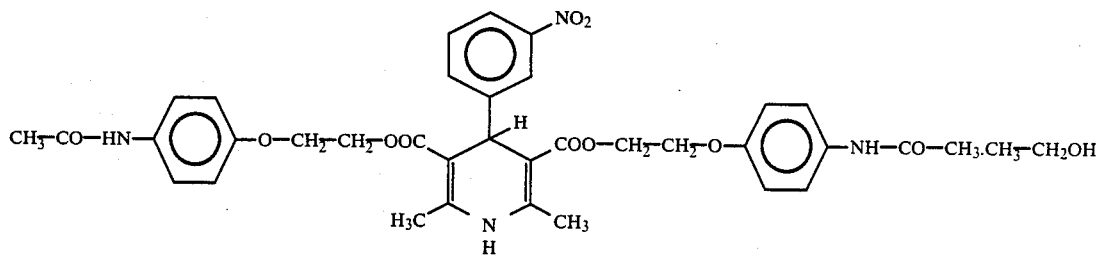

IR spectrum (KBr): ν(cm⁻¹): 3320, 3100, 1700, 1670, 1530, 1510, 1350, 1210, 1120, 1010, 820, 700.

NMR spectrum (δ, CDCl₃): p.p.m: 8.1–6.6 (10H, m); 5.1 (1H, s); 4.4–4 (6H, m); 2.6 (2H, t); 2.3 (6H, s); 2.2 (3H, s); 2.1 (3H, s).

10 g (0.04 moles) of 2-(4-acetylaminophenoxy)ethyl 3-aminocrotonate, 10.04 g (0.04 moles) of 2-(4-acetylaminophenoxy)ethyl acetylacetate and 5.43 g (0.04 moles of 3-nitrobenzaldehyde are heated under reflux in 35 ml of ethanol for 1.5 hours. The solution is then allowed to cool down to room temperature to obtain bis-2-(4-acetylaminophenoxy)ethyl 2,6-dimethyl-4-(3-nitrophenyl)-1,4-dihydropyridine-3,5-dicarboxylate with one molecule of ethanol as a pale yellow powder melting—after recrystallisation in ethanol—at 142°–152° C. The yield is 50% of the theoretical yield.

EXAMPLE 4

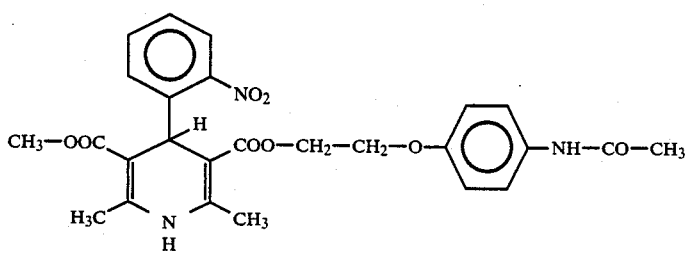

15 g (0.04 moles) of 2-(4-acetylaminophenoxy)ethyl 2-(2-nitrobenzylidene)acetylacetate and 4.19 g (0.04 moles) of methyl 3-aminocrotonate are heated under reflux in 35 ml of ethanol for 10 hours. The solution is then cooled at −5° C. to obtain 2-(4-acetylaminophenoxy)ethyl 2,6-dimethyl-5-methoxycarbonyl-4-(2-nitrophenyl)-1,4-dihydropyridine-3-carboxy as yellow crystals melting—after recrystallisation in ethanol—at 163°–166° C. The yield is 56% of the theoretical yield.

| Analysis for C₂₆H₂₇N₃O₈ | | | |
|---|---|---|---|
| | % C | % H | % N |
| Calculated | 61.29 | 5.35 | 8.25 |
| Found | 61.27 | 5.36 | 7.94 |

| Analysis for C₃₅H₃₆N₄O₁₀·C₂H₆O | | | |
|---|---|---|---|
| | % C | % H | % N |
| Calculated | 61.83 | 5.89 | 7.79 |
| Found | 62.08 | 5.79 | 8.02 |

IR spectrum (KBr): ν(cm⁻¹): 3330, 1690, 1670, 1540, 1520, 1350, 1250, 1120, 720.

NMR spectrum (δ, DMSO-d₆): p.p.m: 9.7 (2H, s); 9 (1H, s); 8–6.6 (12H, m); 5 (1H, s); 4.4–4 (8H, m); 3.4 (2H, q); 2.3 (6H, s); 2 (6H, s); 1.1 (3H, t).

EXAMPLE 6

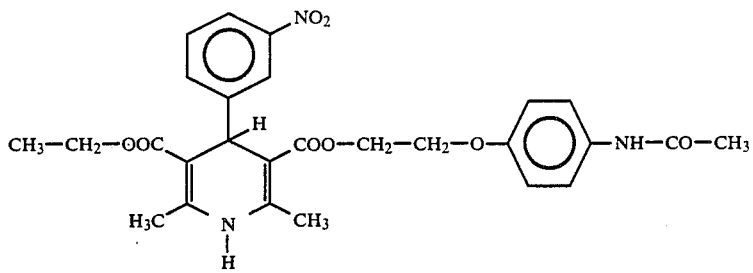

12.28 g (0.03 moles) of 2-(4-acetylaminophenoxy)ethyl 2-(3-nitrobenzylidene)acetylacetate and 3.85 (0.03 moles) of ethyl 3-aminocrotonate are heated under reflux in 30 ml of ethanol for 8 hours. The solution is then cooled to −5° C. to obtain 2-(4-acetylaminophenoxy)ethyl 2,6-dimethyl-5-ethoxycarbonyl-4-(3-nitrophenyl)-1,4-dihydropyridine-3-carboxylate as yellow crystals melting—after recrystallisation in ethanol—at 198°-200° C. The yield is 75% of the theoretical yield.

| Analysis for $C_{27}H_{29}N_3O_8$: | | | |
|---|---|---|---|
| | % C | % H | % N |
| Calculated | 61.94 | 5.58 | 8.03 |
| Found | 61.88 | 5.87 | 7.55 |

IR spectrum (KBr): $\nu(cm^{-1})$: 3360, 3280, 3220, 3080, 1695, 1665, 1530, 1510, 1310, 1240, 1200, 1090, 930, 840, 780, 700.

NMR spectrum (δ, CDCl$_3$): p.p.m: 9.7 (1H, s); 9 (1H, s); 8-6.6 (8H, m); 5 (1H, s); 4.2 (6H, m); 2.4 (6H, s); 2.1 (3H, s); 1.1 (3H, t).

EXAMPLE 7

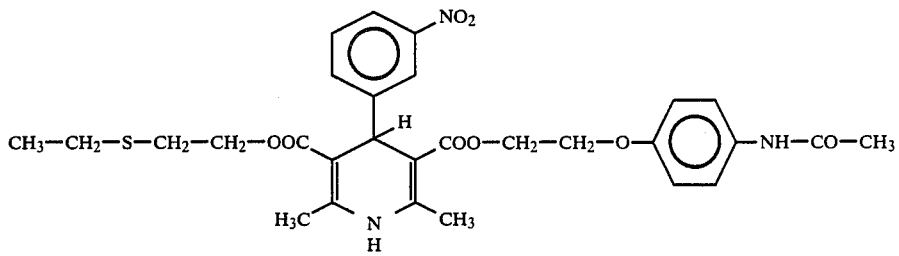

15 g (0.04 moles) of 2-(4-acetylaminophenoxy)ethyl 2-(3-nitrobenzylidene)acetylacetate and 6.88 g (0.04 moles) of 2-ethylthioethyl 3-aminocrotonate were heated under reflux in 35 ml of ethanol for 8 hours. The solution was then cooled to −5° C. to obtain 2-(4-acetylaminophenoxy)ethyl 2,6-dimethyl-5-(2-ethylthioethoxycarbonyl)-4-(3-nitrophenyl)-1,4-dihydropyridine-3-carboxylate as a yellow powder melting—after recrystallisation in ethanol—at 100°-104° C. The yield is 60% of the theoretical yield.

| Analysis for $C_{29}H_{33}N_3O_8S$: | | | | |
|---|---|---|---|---|
| | % C | % H | % N | % S |
| Calculated | 59.68 | 5.70 | 7.20 | 5.49 |
| Found | 59.19 | 6.02 | 7.19 | 5.90 |

IR spectrum (KBr): $\nu(cm^{-1})$: 3440, 3340, 3150, 1730, 1700, 1560, 1380, 1250, 1150, 860, 740.

NMR spectrum (δ, SDCl$_3$): p.p.m.: 8-6.6 (10H, m); 5.1 (1H, s); 4.4-4 (6H, m); 2.6 (4H, m); 2.3 (6H, s); 2.1 (3H, s); 1.2 (3H, t).

EXAMPLE 8

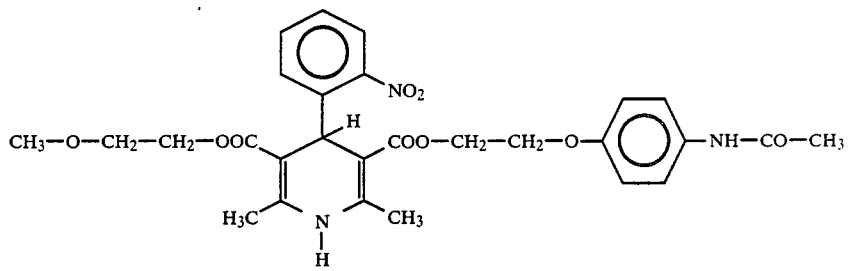

15 g (0.04 moles) of 2-(4-acetylaminophenoxy)ethyl 2-(2-nitrobenzylidene)acetylacetate and 5.79 g (0.04 moles) of 2-methoxyethyl 3-aminocrotonate are heated under reflux in 35 ml of ethanol for 10 hours. The solution is then allowed to cool down to room temperature to obtain 2-(4-acetylaminophenoxy)ethyl 2,6-dimethyl-5-(2-methoxyethoxycarbonyl)-4-(2-nitrophenyl)-1,4-dihydropyridine-3-carboxylate as yellow crystals melting with decomposition—after recrystallisation in ethanol—at 94°-105° C. The yield is 84% of the theoretical yield.

| Analysis for $C_{28}H_{31}N_3O_9$ | | | |
|---|---|---|---|
| | % C | % H | % N |
| Calculated | 60.75 | 5.64 | 7.59 |
| Found | 60.48 | 5.64 | 7.59 |

IR spectrum (KBr): $\nu(cm^{-1})$: 3350, 1705, 1540, 1520, 1210, 1110, 835, 720.

NMR spectrum ($\delta$, CDCl$_3$): p.p.m: 7.9–6.4 (10H, m); 5.8 (1H, s); 4.9 (1H, h); 4.3 (2H, sl); 4.1 (2H, sl); 3.7 ($\frac{1}{2}$ 2H, q); 2.3 (6H, d); 2.1 (3H, s); 1.3–0.9 (6H+3H, d+t).

EXAMPLE 10

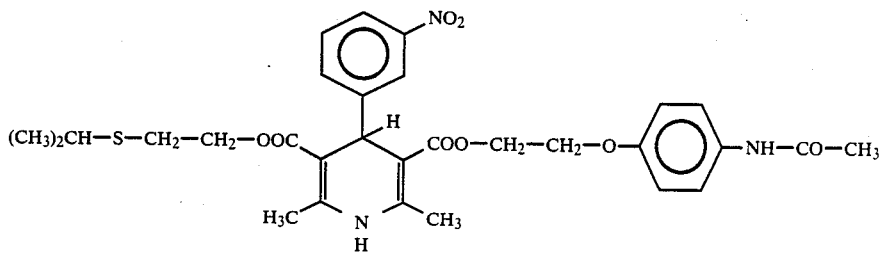

IR spectrum (KBr): $\nu(cm^{-1})$: 3300, 1710, 1655, 1540, 1520, 1250, 1200, 890, 830, 720.

NMR spectrum ($\delta$, DMSO-d$_6$): p.p.m: 9.8 (1H, s); 9 (1H, s); 7.6–6.6 (8H, m); 5.6 (1H, s); 4.1 (6H, m); 3.4 (2H, m); 3.1 (3H, s); 2.2 (5H,s); 2 (3H, s).

EXAMPLE 9

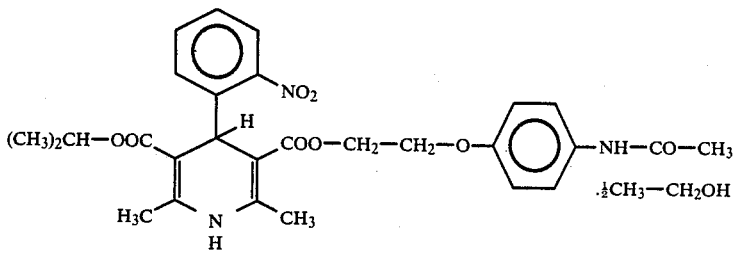

15 g (0.04 moles) of 2-(4-acetylaminophenoxy)ethyl 2-(2-nitrobenzylidene)acetylacetate and 5.21 g (0.04 moles) of isopropyl 3-aminocrotonate are heated under reflux in 35 ml of ethanol for 10 hours. The solution is then cooled to −5° C. to obtain 2-(4-acetylaminophenoxy)ethyl 2,6-dimethyl-5-isopropoxycarbonyl-4-(2-nitrophenyl)-1,4-dihydropyridine-3-carboxylate with half a molecule of ethanol as yellow crystals melting—after recrystallisation in ethanol—at 103°–112° C. The yield is 35% of the theoretical yield.

| Analysis for $C_{28}H_{31}N_3O_8.\frac{1}{2}C_2H_6O$ | | | |
|---|---|---|---|
| | % C | % H | % N |
| Calculated | 62.13 | 6.11 | 7.50 |
| Found | 62.05 | 5.98 | 7.82 |

12 g (0l03 moles) of 2-(4-acetylaminophenoxy)ethyl 2-(3-nitrobenylidene)acetylacetate and 5.92 g (0.03 moles) of 2-isopropylthioethyl 3-aminocrotonate are heated under reflux in 30 ml of ethanol for 8 hours. The solution is then cooled to −5° C. to obtain 2-(4-acetylaminophenoxy)ethyl 2,6-dimethyl-5-(2-isopropyl-thioethoxycarbonyl)-4-(3-nitrophenyl)-1,4-dihydropyridine-3-carboxylate as yellow crystals melting—after recrystallisation in aqueus ethanol—at 142°–144° C. The yield was 42% of the theoretical yield.

| Analysis for $C_{30}H_{35}N_3S$ | | | | |
|---|---|---|---|---|
| | % C | % H | % N | % S |
| Calculated | 60.29 | 5.90 | 7.03 | 5.36 |
| Found | 60.35 | 6.10 | 6.97 | 5.65 |

IR spectrum (KBr): $\nu(cm^{-1})$: 3300, 3260, 3100, 1670, 1620, 1530, 1510, 1350, 1210, 1120, 1020, 920, 820, 750, 700.

NMR spectrum ($\delta$, CDCl$_3$+DMSO-d$_6$): p.p.m.: 9.2 (1H, s); 8.3 (1H, s); 8–6.6 (8H, m); 5.1 (1H, s); 4.4–4 (6H, m); 3–2.5 (3H, m); 2.35 (6H, s); 2.1 (3H, s); 1.2 (6H, d).

EXAMPLE 11

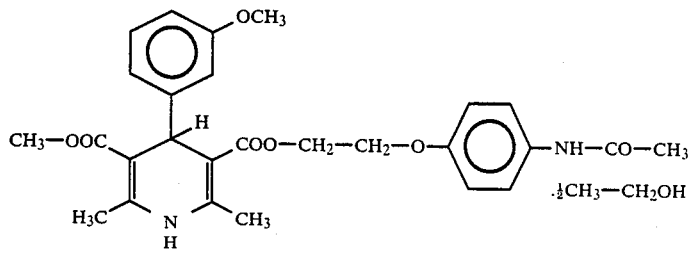

10 g (0.04 moles) of methyl 2-(3-methoxybenzylidene-)acetylacetate and 11.88 g (0.04 moles) of 2-(4-acetylaminophenoxy)ethyl 3-aminocrotonate are heated under reflux in 50 ml of ethanol for 8 hours. The solution is then cooled to −5° C. to obtain 2-(4-acetylaminophenoxy)ethyl 2,6-dimethyl-5-methoxycarbonyl-4-(3-methoxyphenyl)-1,4-dihydropyridine-3-carboxylate with half a molecule of ethanol as white needles melting—after recrystallisation in ethanol—at 88°-92° C. The yield is 50% of the theoretical yield.

| Analysis for $C_{27}H_{30}N_2O_7 \cdot \frac{1}{2}C_2H_6O$ | | | |
|---|---|---|---|
| | % C | % H | % N |
| Calculated | 64.98 | 6.43 | 5.41 |
| Found | 64.80 | 6.68 | 5.44 |

IR spectrum (KBr): $\nu(cm^{-1})$: 3400, 1710, 1670, 1670, 1520, 1500, 1220, 1120, 1055, 830, 780, 720.

NMR spectrum ($\delta$, DMSO-$d_6$): p.p.m.: 9.7 (1H, s); 8.8 (1H, s); 7.6–6.6 (8H, m); 4.9 (1H, s); 4.2 (4H, m); 3.65 (3H, s); 3.55 (3H, s); 2.3 (6H, s); 2 (3H, s); 1.1 ($\frac{1}{2}$ 3H,t).

EXAMPLE 12

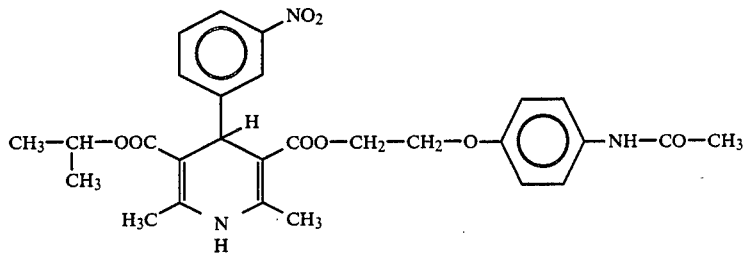

15 g (0.04 moles) of 2-(4-acetylaminophenoxy)ethyl 2-(3-nitrilobenzylidene)acetylacetate and 5.21 g (0.04 moles) of isopropyl 3-aminocrotonate are heated under reflux in 35 ml of ethanol for 8 hours. 15 ml of the solvent are then evaporated, and the remaining fraction is cooled to −5° C. to obtain 2-(4-acetylaminophenyl)ethyl 2,6-dimethyl-5-isopropoxycarbonyl-4-(3-nitrophenyl)-1,4-dihydropyridine-3-carboxylate as a pale yellow powder melting—after recrystallisation in ethanol—at 146°-148° C. The yield is 50% of the theoretical yield.

| Analysis for $C_{28}H_{31}N_3O_8$ | | | |
|---|---|---|---|
| | % C | % H | % N |
| Calculated | 62.56 | 5.81 | 7.82 |
| Found | 62.89 | 5.99 | 8.03 |

IR spectrum (KBr): $\nu(cm^{-1})$: 3400, 3300, 3080, 1700, 1675, 1530, 1510, 1350, 1240, 1210, 1100, 1070, 840, 790, 700.

NMR spectrum ($\delta$, CDCl$_3$): p.p.m.: 8–6.5 (10H, m); 5 (1H+1H, s+m); 4.3 (2H, m); 4.05 (2H, m); 2.3 (6H, s); 2.1 (3H, s); 1.1 (6H, q).

EXAMPLE 13

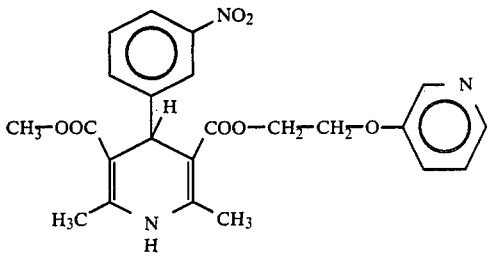

25 g (0.07 moles) of 2-(N-nicotinoylamino)ethyl 2-(3-nitrobenzylidene)acetylacetate and 7.51 g (0.07 moles) of methyl 3-aminocrotonate are heated uner reflux in 70 ml of ethanol for 45 minute. The solution is the cooled to room temperature to obtain 2-(N-nicotinoylamino)ethyl 2,6-dimethyl-5-methoxycarbonyl-4-(3-nitrophenyl)-1,4-dihydropyridine-3-carboxylate as yellow crystals melting—after recrystallisation in ethanol—at 207°-209° C. The yield is 70% of the theoretical yield.

| Analysis for $C_{24}H_{24}N_4O_7$ | | | |
|---|---|---|---|
| | % C | % H | % N |
| Calculated | 60.00 | 5.03 | 11.66 |
| Found | 59.99 | 5.20 | 11.20 |

IR spectrum (KBr): $\nu(cm^{-1})$: 3340, 3220, 3080, 2960, 1700, 1670, 1510, 1350, 1210, 1120, 1040, 780, 750, 700.

NMR spectrum ($\delta$, DMSO-$d_6$): p.p.m.: 9.2–7.3 (10H,m); 5.1 (1H, s); 4.2 (2H, m); 3.6 (5H, s); 2.4 (6H, s).

EXAMPLE 14

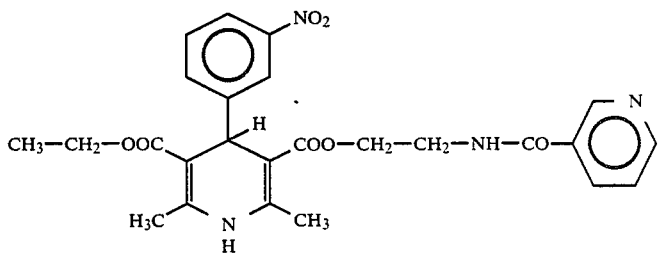

10 g (0.03 moles) of 2-(N-nicotinoylamino)ethyl 2-(3-nitrobenzylidene)acetylacetate and 3.37 g (0.03 moles) of ethyl 3-aminocrotonate are heated uner reflux in 35 ml of ethanol for 8 hours. 15 ml of the solvent are then evaporated and the remaining fraction is cooled to −5° C. to obtain 2-(N-nicotinoylamino)ethyl 2,6-dimethyl-5-ethoxycarbonyl-4-(3-nitrophenyl-1,4-dihydropyridine-3-carboxylate as yellow crystals melting—after recrystallisation in ethanol—153°-155° C. The yield is 32% of the theoretical yield.

| Analysis for C25H26N4O7 | | | |
|---|---|---|---|
| | % C | % H | % N |
| Calculated | 60.72 | 5.30 | 11.33 |
| | 61.02 | 5.46 | 11.53 |

IR spectrum (KBr): $\nu(cm^{-1})$: 3300, 3220, 3080, 1690, 1640, 1530, 1490, 1145, 1200, 1090, 780, 740, 700.

NMR spectrum (δ, SDCl3+DMSO-d6): p.p.m.: 9–7.2 (10H, m); 5.1 (1H, s); 4.3–3.4 (6H, m); 2.35 (6H, s); 1.2 (3H, t).

EXAMPLE 15

IR spectrum (KBr): $\nu(cm^{-1})$: 3380, 3250, 3080, 1685, 1539, 1490, 1350, 1220, 1120, 1020, 830, 740, 710, 680.

NMR spectrum (δ, CDCl3+DMSO-d6): p.p.m.: 13.6 (1H, sl); 9.4–7.2 (10, m); 5.05 (1H, s); 4,2 (4H, m); 3.6 (2H, m); 2.6 (2H, t); 2.4 (6H, s); 2.1 (3H, s).

EXAMPLE 16

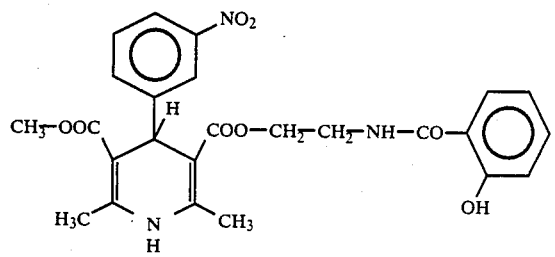

14.15 g (0.06 moles) of methyl 2-(3-nitrobenzylidene)acetylacetate and 15 g (0.06 moles) of 2-(N-salicylamido)ethyl 3-aminocrotonate are heated under reflux in 55 ml of ethanol for 6 hours. The solvent is then evaporated, and the remaining oil dissolved in 10 ml of boiling methanol. This solution is cooled to room temperature to obtain 2-(N-salicylamido)ethyl 2,6-dimethyl-5-methoxycarbonyl-4-(3-nitrophenyl)-1,4-dihydropyridine-3-carboxylate as yellow crystals melting—after recrystallisation in ethanol—at 165°-170° C. The yield is 83% of the theoretical yield.

| Analysis for C25H25N3O8 | | | |
|---|---|---|---|
| | % C | % H | % N |
| Calculated | 60.60 | 5.09 | 8.48 |
| Found | 60.54 | 5.12 | 8.70 |

IR spectrum (KBr) $\nu(cm^{-1})$: 3460, 3380, 1710, 1660, 1545, 1490, 1360, 1210, 1130, 1095, 755, 705.

NMR spectrum (δ, CDCl3): p.p.m.: 12.3 (1H, s); 8.6–6.7 (10H, m); 5.1 (1H, s); 4.2 (2H, m); 3.55 (5H, sd); 2.35 (6H, s).

EXAMPLE 17

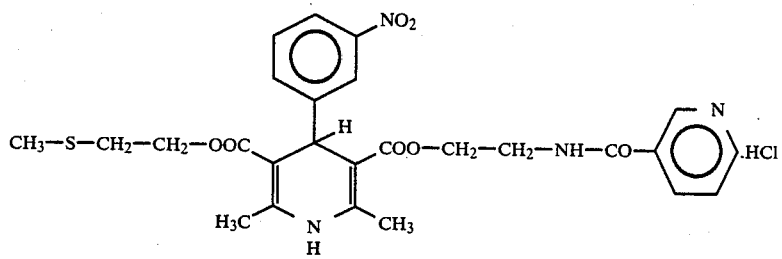

10.79 g (0.03 moles) of 2-(N-nicotinyolamino)ethyl 2-(3-nitrobenzylidene)acetylacetate and 4.93 g (0.03 moles) of 2-methylthioethyl 3-aminocrotonate are heated under reflux in 30 ml of ethanol for 10 hours. The solvent is then evaporated and an orange oil is obtained which is transformed into the corresponding chlorhydrate by first dissolving the oil in 100 ml of absolute ethanol and then by adding 100 ml of ethyl ether saturated with hydrogen chloride. By evaporating the solvent the chlorhydrate of 2-(N-nicotinoylamino)ethyl 2,6-dimethyl-5-(2-methylthioethoxycarbonyl)-4-(3-nitrophenyl)-1,4-dihydropyridine-3-carboxylate is obtained which after recrystallisation from ethanol-ether forms yellow crystals melting and decomposing at the same time at 120°-130° C. The yield is 25% of the theoretical yield

| Analysis for C26H28N4O7S.HCl | | | | | |
|---|---|---|---|---|---|
| | % C | % H | % N | % S | % Cl |
| Calculated | 54.12 | 5.07 | 9.71 | 5.56 | 6.14 |
| Found | 54.33 | 5.18 | 9.89 | 4.65 | 6.24 |

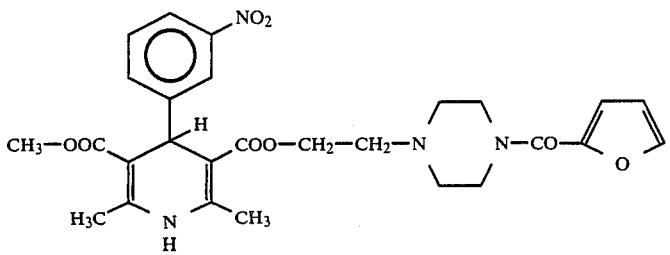

12 g (0.05 moles) of methyl 2-(3-nitrobenzylidene)acetylacetate and 14.8 g (0.05 moles) of 2-(4-(2-furoyl)-1-piperazinyl)ethyl 3-aminocrotonate are heated under reflux in 45 ml of ethanol for 8 hours. The solvent is then evaporated and the removing oil is transformed into the corresponding chlorhydrate by dissolution in 100 of ethyl ether saturated with hydrogen chloride. The solvent is evaporated and the residue triturated with boiling ethanol to obtain the chlorhydrate of 2-(4-(2-furoyl)-1-piperazinyl)ethyl 2,6-dimethyl-5-methoxycarbonyl-4-(3-nitrophenyl)-1,4-dihydropyridine-3-carboxylate as a pale yellow powder melting while at the same time decomposing at 237°–240° C. The yield is 40% of theoretical yield.

| Analysis for $C_{27}H_{30}N_4O_8HCl$ | | | | |
|---|---|---|---|---|
| | % C | % H | % N | % Cl |
| Calculated | 56.40 | 5.43 | 9.74 | 6.17 |
| Found | 56.71 | 5.60 | 10.42 | 6.41 |

IR spectrum (KBr): $\nu(cm^{-1})$: 3240, 3120, 2600, 2530, 1710, 1670, 1540, 1495, 1360, 1220, 1135, 890, 760, 710.

NMR spectrum ($\delta$, DMSO-$d_6$): p.p.m.: 9.2 (1H, sl); 8–6.5 (8H, m); 5 (1H, s); 4.4 (4H, sl); 3.7–3 (3H+8H, m); 2.3 (6H, d).

EXAMPLE 18 tion is the cooled to −5° C. to obtain 2-(4-(2-furoyl)-1-piperazinyl)ethyl 2,6-dimethyl-5-ethoxycarbonyl-4-(3-nitrophenyl)-1,4-dihydropyridine-3-carboxylate as yellow crystals melting—after recrystallisation in ethanol—at 149°–152° C. The yield is 65% of the theoretical yield.

| Analysis for $C_{28}H_{32}N_4O_8$ | | | |
|---|---|---|---|
| | % C | % H | % N |
| Calculated | 60.86 | 5.84 | 10.14 |
| Found | 61.14 | 5.97 | 10.08 |

IR spectrum (KBr): $\nu(cm^{-1})$: 3280, 3220, 3100, 2980, 1700, 1620, 1540, 1500, 1360, 1280, 1210, 1110, 1030, 790, 750, 720.

NMR spectrum ($\delta$,CDCl$_3$): p.p.m.: 8.1–6.4 (8H, m); 5.1 (1H, s); 4.2 (4H, m); 3.7 (4H, m); 2.7–2.2 (6H+6H, m+s); 1.2 (3H, t).

EXAMPLE 19

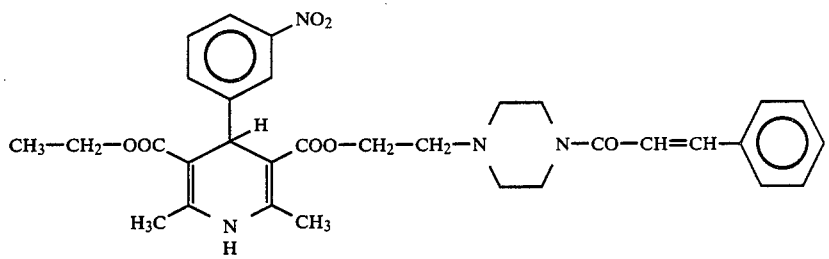

11.78 g (0.04 moles) of ethyl 2-(3-nitrobenzylidene)acetylacetate and 15.37 g (0.04 moles) of 2-(4-cinnamoyl-1-piperzinyl)ethyl 3-aminocrotonate are heated under reflux in 45 ml of ethanol for 8 hours. The solution is the cooled to −5° C. to obtain 2-(4-cinnamoyl-1-piperazinyl)ethyl 2,6-dimethyl-5-ethoxycarbonyl-4-(3-nitrophenyl)-1,4-dihydropyridine-3-carboxylate as yel-

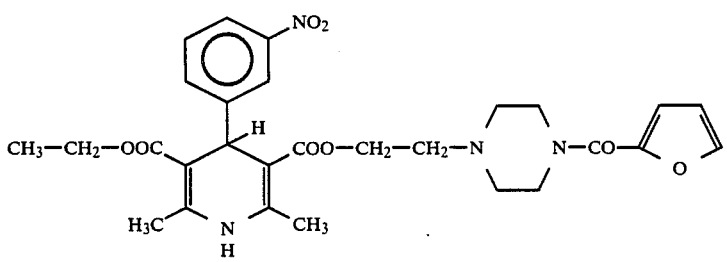

17.32 g (0.07 moles) of ethyl 2-(3-nitrobenzylidene)acetylacetate and 20.22 g (0.07 moles) of 2-(4-(2-furoyl)-1-piperazinyl)ethyl 3-aminocrotonate are heated under reflux in 60 ml of ethanol for 7 hours. The solulow crystals melting—after recrystallisation in ethanol—at 164°–172° C. The yield is 56% of the theoretical yield.

| Analysis for $C_{32}H_{36}N_4O_7$ | | | |
|---|---|---|---|
| | % C | % H | % N |
| Calculated | 65.29 | 6.16 | 9.52 |
| Found | 65.49 | 6.20 | 9.78 |

IR spectrum (Kbr): $\nu(cm^{-1})$: 3300, 3250, 3120, 1710, 1650, 1600, 1540, 1360, 1280, 1210, 1100, 785, 760, 715.

NMR spectrum ($\delta$, $CDCl_3$): p.p.m.: 8.2–6.7(12H, m); 5.1(1H, s); 4.2(4H, m); 3.6(4H, s); 2.6–2.2(6H+6H, m+s); 1.2(3H, t).

EXAMPLE 20

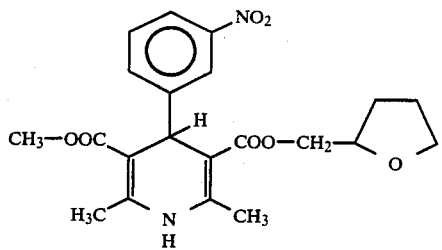

15 g (0.05 moles) of 2-tetrahydrofurfuryl 2-(3-(nitrobenzylidene)acetylacetate and 5.41 g (0.05 moles) of methyl 3-aminocrotonate are heated under reflux in 50 ml of ethanol for 8 hours. The solution is then cooled down to $-5°$ C. to obtain 2-tetrahydrofurfuryl 2,6-dimethyl-5-methoxycarbonyl-4-(3-nitrophenyl)-1,4-dihydropyridine-3-carboxylate as yellow crystals melting—after recrystallisation in ethanol—at 135°–140° C. The yield is 50% of the theorical yield.

| Analysis for $C_{21}H_{24}N_2O_7$ | | | |
|---|---|---|---|
| | % C | % H | % N |
| Calculated | 60.57 | 5.81 | 6.73 |
| Found | 60.51 | 5.99 | 6.39 |

IR spectrum (KBr): $\nu(cm^{-1})$: 3470, 3100, 2950, 2870, 1710, 1650, 1530, 1480, 1345, 1220, 1120, 1020, 825, 780, 740.

NMR spectrum ($\delta$, $CDCl_3$): p.p.m.: 8.1–7.2(4H, m); 6.8(1H, s); 5.1(1H, s); 4.1(3H, sd); 3.9–3.6(2H+3H, m+s); 2.35(6H, s); 1.8(4H, m).

EXAMPLE 21

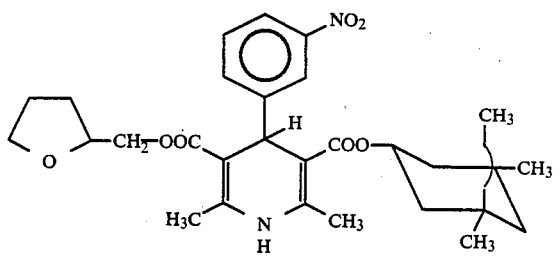

15 g (0.08 moles) of 2-tetrahydrofurfuryl 3-aminocrotonate, 18.33 g (0.08 moles) of 3,3,5-trimethycyclohexyl acetylacetate and 12.24 g (0.08 moles) of nitrobenzaldehyde are heated under reflux in 65 ml of ethanol for 12 hours. 35 ml of water are then added to the mixture, which is cooled to $-5°$ C. A yellow oil is thus obtained which is separated by decanting and dried in a desiccator. 3,3,5-trimethylcyclohexyl 2,6-dimethyl-4-(3-nitrophenyl)-5-(2-tetrahydrofurfuryloxycarbonyl)-1,4-dihydropyridine-3-carboxylate is obtained as yellow crystals melting—after recrystallisation in ethanol—at 159°–162° C. The yield is 304 of the theoretical yield.

| Analysis for $C_{29}H_{38}N_2O_7$ | | | |
|---|---|---|---|
| | % C | % H | % N |
| Calculated | 66.14 | 7.27 | 5.32 |
| Found | 66.41 | 7.57 | 5.23 |

IR spectrum (KBr): $\nu(cm^{-1})$: 3380, 2950, 1700, 1520, 1490, 1345, 1200, 1090, 790, 740, 710.

NMR spectrum ($\delta$, $CDCl_3$): p.p.m.: 8.1–7.2(4H, m); 6.5(1H, s); 5.2(1H, d); 5(1H, s); 4.1–3.8(s+t, 3H+2H); 2.3(6H, d); 2–0.6(m, 2OH).

EXAMPLE 22

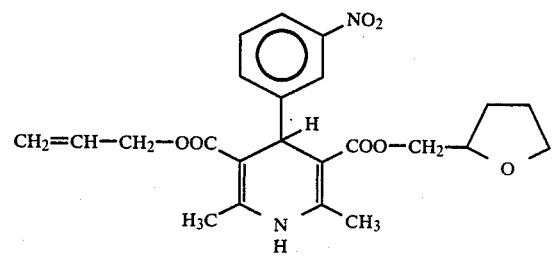

15 g (0.08 moles) of 2-tetrahydrofurfuryl 3-aminocrotonate, 11.51 g (0.08 moles) of ally acetylacetate and 12.24 g (0.08 moles) of 3-nitrobenzaldehyde are heated under reflux in 65 ml of ethanol for 12 hours. 30 ml of the solvent are then evaporated and the remaining fraction is cooled to obtain a product which is purified by chromatography on a column of cilica gel-60/benzene. The elution is carried out using a 9:1 mixture of benzene and ethyl acetate to obtain 2-tetrahydrofurfuryl 5-allyloxycarbonyl-2,6-dimethyl-4-(3-nitrophenyl)-1,4-dihydropyridine-3-carboxylate as yellow crystals melting at 129°–131° C. The yield is 26% of the theoretical yield.

| Analysis for $C_{23}H_{26}N_2O_7$ | | | |
|---|---|---|---|
| | % C | % H | % N |
| Calculated | 62.43 | 5.92 | 6.33 |
| Found | 62.67 | 5.87 | 6.53 |

IR analysis (KBr): $\nu(cm^{-1})$: 3340, 3260, 2950, 2880, 1700, 1660, 1530, 1350, 1210, 1090, 1020, 780, 750, 700.

NMR spectrum ($\delta$, $CDCl_3$): p.p.m: 8.1–7.2(4H, m); 6.6(1H, s); 5.7(1H, m); 5.3–4.9(4H, m); 4.5(2H, d); 4.1(2H, s); 3.8(2H, td); 2.4(6H, s); 1.9(4H, m).

EXAMPLE 23

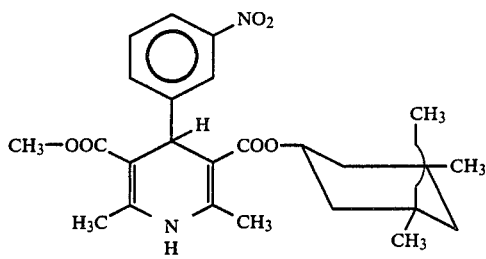

15 g (0.06 moles) of methyl 2-(3-nitrobenzylidene)acetylacetate and 13.56 g (0.06 moles) of 3,3,5-trimethylcyclohexyl 3-aminocrotonate are heated under reflux in 60 ml of ethanol for 8 hours. 30 ml of solvent are then evaporated, and the remaining fraction is cooled to −5° C. to obtain 3,3,5-trimethylcyclohexyl 2,6-dimethyl-5-methoxycarbonyl-4-(3-nitrophenyl)-1,4-dihydropyridine-3-carboxylate as pale yellow crystals melting—after recrystallisation in ethanol—at 137°–140° C.

21.87 g (0.06 moles) of 3,3,5-trimethylcyclohexyl 2-(3-nitrobenzylidene)acetylacetate and 7.84 g (0.06 moles) of ethyl 3-aminocrotonate are heated under reflux in 60 ml of ethanol for 8 hours. The solution is then cooled to −5° C. to obtain 3,3,5-trimethylcyclohexyl 2,6-dimethyl-5-ethoxycarbonyl-4-(3-nitrophenyl)-1,4-dihydropyridine-3-carboxylate as yellow crystals melting—after recrystallisation in ethanol—at 125°–129° C. The yield is 37% of the theoretical yield.

| Analysis for $C_{26}H_{34}N_2O_6$ | | | |
|---|---|---|---|
|  | % C | % H | % N |
| Calculated | 66.36 | 7.28 | 5.95 |
| Found | 66.10 | 7.66 | 5.98 |

IR spectrum (KBr): $\nu(cm^{-1})$: 3380, 2940, 1700, 1520, 1470, 1340, 1270, 1200, 1090, 880, 780, 740, 710.

NMR spectrum ($\delta$, $CDCl_3$): p.p.m.: 8.3–7.3(4H, m); 6.7(1H, s); 5.3(1H, s); 5.1(1H, sl); 4.2(2H, q); 2.4–0.8(25H, m).

EXAMPLE 25

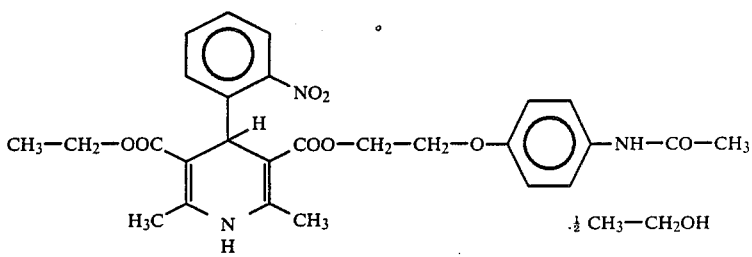

The yield is 35% of the theoretical yield.

| Analysis for $C_{25}H_{32}N_2O_6$ | | | |
|---|---|---|---|
|  | % C | % H | % N |
| Calculated | 65.77 | 7.07 | 6.14 |
| Found | 65.71 | 7.35 | 6.07 |

IR spectrum (KBr): $\nu(cm^{-1})$: 3360, 2960, 2920, 1680, 1665, 1540, 1490, 1360, 1230, 1130, 1020, 780, 760, 700.

NMR spectrum ($\delta$, $CDCl_3$): p.p.m.: 8.1–7.2(4H, m); 6.5(1H, m); 5.2(1H, s); 5(1H, sl); 3.6(3H, s); 2.35(6H, d); 1.8–0.7(16H, m).

EXAMPLE 24

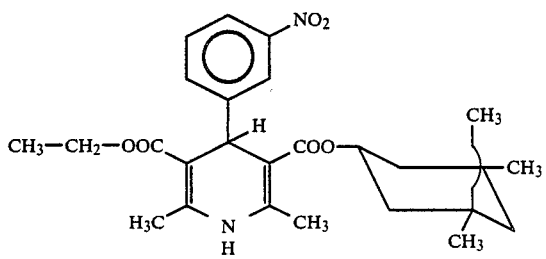

8.02 g (0.03 moles) of ethyl 2-(2-nitrobenzylidene)acetylacetate and 9.65 g (0.03 moles) of 2-(4-acetylaminophenoxy)ethyl 3-aminocrotonate are heated under reflux in 40 ml of ethanol for 8 hours. The solution is then cooled to −5° C. to obtain 2-(4-acetylaminophenoxy)ethyl 2,6-dimethyl-5-ethoxycarbonyl-4-(2-nitrophenyl)-1,4-dihydropyridine-3-carboxylate with half a molecule of ethanol as yellow crystals melting—after recrystallisation in ethanol—at 96°–108° C. The yield is 57% of the theoretical yield.

| Analysis for $C_{27}H_{29}N_3O_8 \cdot \frac{1}{2} C_2H_6O$ | | | |
|---|---|---|---|
|  | % C | % H | % N |
| Calculated | 61.53 | 5.90 | 7.69 |
| Found | 61.08 | 6.07 | 7.45 |

IR spectrum (KBr): $\nu(cm^{-1})$: 3380, 3000, 1700, 1540, 1520, 1320, 1220, 1120, 1025, 835, 760, 715.

NMR spectrum ($\delta$, $CDCl_3$): p.p.m.: 8.2–6.5(9H, m) 5.8(1H, s); 4.4–3.8(7H, m) 2.3(6H, s); 2.1(3H, s); 1.1(4.5H, t).

EXAMPLE 26

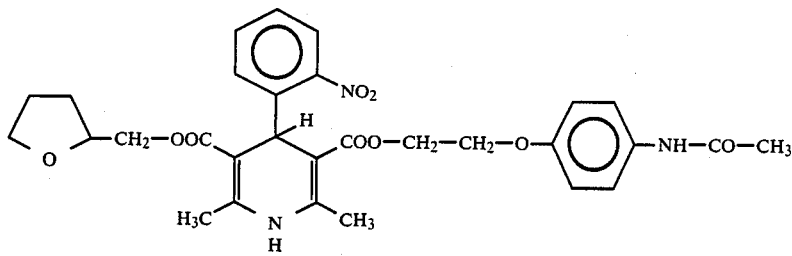

15 g (0.05 moles) of 2-tetrahydrofurfuryl 2-(2-nitrobenzylidene)acetylacetate and 13.07 g (0.05 moles) of 2-(4-acetylaminophenoxy)ethyl 3-aminocrotonate are heated under reflux in 50 ml of ethanol for 8 hours. The solution is then cooled to room temperature to obtain 2-(4-acetylaminophenoxy)ethyl 2,6-dimethyl-4-(2-nitrophenyl)-5-(2-tetrahydrofurfuryloxycarbonyl)-1,4-dihydropyridine-3-carboxylate as yellow needles melting—after recrystallisation in ethano—at 146°-150° C. The yield is 57% of the theoretical yield.

| Analysis for $C_{30}H_{33}N_3O_9$ | | | |
|---|---|---|---|
| | % C | % H | % N |
| Calculated | 62.17 | 5.74 | 7.25 |
| Found | 61.90 | 5.43 | 6.99 |

IR spectrum (KBr): $\nu(cm^{-1})$: 3310, 2980, 1705, 1670, 1540, 1520, 1500, 1250, 1200, 1120, 1100, 1020, 830, 780, 750, 710.

NMR spectrum ($\delta$, DMSO-$d_6$): p.p.m.: 9.7(1H, s); 8.9(1H, s); 7.7-6.6(8H, m); 4.3-3.3(9H, m); 2.2(8H, s); 2.0(3H, s); 1.8-1.3(4H, m).

phenyl)-1,4-dihydropyridine-3-carboxylate as yellow slightly hygroscopic crystals melting—after recrystallisation in absolute alcohol—at 112°-121° C. The yield is 66% of the theoretical yield.

| Analysis for $C_{34}H_{34}N_4O_{10}$ | | | |
|---|---|---|---|
| | % C | % H | % N |
| Calculated | 62.00 | 5.20 | 8.51 |
| | 62.33 | 4.87 | 8.46 |

IR spectrum (KBr): $\nu(cm^{-1})$: 3360, 2960, 1700, 1650, 1600, 1540, 1520, 1490, 1350, 1250, 1210, 1130, 1100, 1020, 830, 780, 755, 715.

NMR spectrum ($\delta$, CDCl$_3$+DMSO-$d_6$): p.p.m.: 12.2(1H, s); 9.4(1H, s); 8.6-6.5(14H, m); 5(1H, s); 4.4-3.8(6H, m); 3.8-3.3(2H, m); 2.3(6H, s); 2.05(3H, s).

EXAMPLE 28

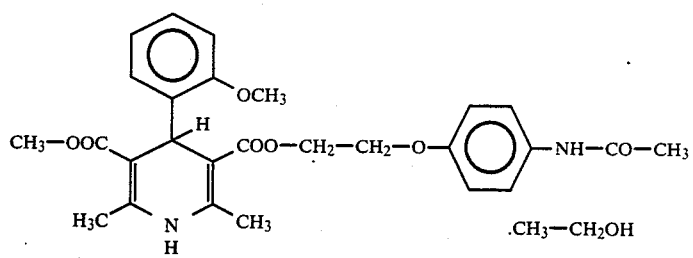

15 g (0.05 moles) of 2-(4-acetylaminophenoxy)ethyl 3-aminocrotonate and 12.63 g (0.05 moles) of methyl 2-(2-methoxybenzylidene)acetylacetate are heated under reflux in 60 ml of ethanol for 8 hours. The solution is then cooled to −5° C. to obtain 2-(4-acetylaminophenoxy)ethyl 2,6-dimethyl-5-methoxycar-

EXAMPLE 27

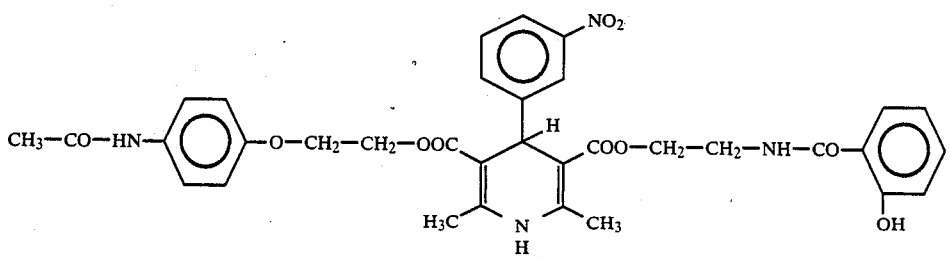

13.05 g (0.05 moles) of 2-(N-salicylamido)ethyl 3-aminocrotonate and 20.36 g (0.05 moles) of 2-(4-acetylaminophenoxy)ethyl 2-(3-nitrobenzylidene)acetylacetate are heated under reflux in 50 ml of absolute alcohol for 8 hours. The solution is the cooled to −5° C. to obtain 2-(N-salicylamido)ethyl 5-(2-(4-acetylaminophenoxy)ethoxycarbonyl)-2,6-dimethyl-4-(3-nitrobonyl-4-(2-methoxyphenyl)-1,4-dihydropyridine-3-carboxylate with one molecule of ethanol as a white slightly yellowish powder melting—after recrystallisation in ethanol—at 98°-101° C. The yield is 55% of the theoretical yield.

| Analysis for $C_{27}H_{30}N_2O_7 \cdot C_2H_6O$ | | | |
|---|---|---|---|
| | % C | % H | % N |
| Calculated | 64.43 | 6.71 | 5.18 |
| Found | 64.66 | 7.00 | 5.19 |

IR spectrum (KBr): $\nu(cm^{-1})$: 3330, 3300, 3100, 1710, 1680, 1540, 1520, 1350, 1250, 1210, 1105, 935, 840, 715.

NMR spectrum ($\delta$, DMSO-$d_6$): p.p.m.: 9.7(1H, sd); 8.9(1H, sl); 7.7–6.5(14H, m); 5.65(1H, sd); 4.4–3.85(8H, sd); 3.4(2H, m); 2.4–1.9(6H+6H, s+s); 1.1(3H, t).

EXAMPLE 30

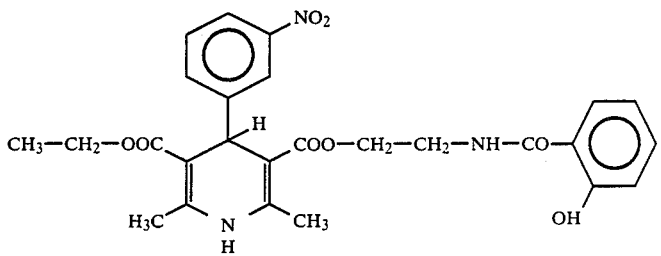

IR analysis (Kbr): $\nu(cm^{-1})$: 3360, 3100, 2960, 1685, 1520, 1495, 1310, 1245, 1210, 1120, 1020, 830, 760.

NMR spectrum ($\delta$, CDCl$_3$): p.p.m.: 8.4(1H, s); 7.6–6.5(10H, m); 5.3(1H, s); 4.3–3.9(4H, m); 3.8–3.4(3H+3H+2H, s+sd); 2.2–2.05(6H+3H, s+s); 1.2(3H, t).

EXAMPLE 29

15 g (0.06 moles) of 2-(N-salicylamido)ethyl 3-aminocrotonate and 14.94 g (0.06 moles) of ethyl 2-(3-nitrobenzylidene)acetylacetate are heated under reflux in 55 ml of ethanol for 8 hours. The solution is then evaporated, 5 ml of methanol are added to the residue, and the mixture is cooled to −5° C. to obtain 2-(N-salicylamido)ethyl 2,6-dimethyl-5-ethoxycarbonyl-4-(3-nitrophenyl)-1,4-dihydropyridine-3-carboxylate as a

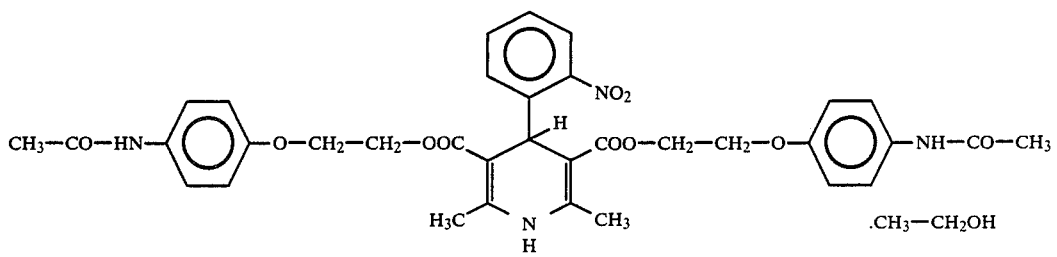

20 g (0.05 moles) of 2-(4-acetylaminophenoxy)ethyl 2-(2-nitrobenzylidene)acetylacetate and 13.5 g (0.05 moles) of 2-(4-acetylaminophenoxy)ethyl 3-aminocrotonate are heated under refulx in 50 ml of ethanol for 2 hours. The solution is then cooled to room temperature to obtain bis-2-(4-acetylaminophenoxy)ethyl 2,6-dimethyl-4-(2-nitrophenyl)-1,4-dihydropyridine-3,5-dicarboxylate with one molecule of ethanol as yellow crystals melting—after recrystallisation in ethanol—at 148°–154° C. The yield is 46% of the theoretical yield.

| Analysis for $C_{35}H_{36}N_4O_{10} \cdot C_2H_6O$ | | | |
|---|---|---|---|
| | % C | % H | % N |
| Calculated | 61.83 | 5.89 | 7.79 |
| Found | 61.49 | 6.07 | 7.85 | yellow powdre melting at 127–130. The yield is 86% of the theoretical yield.

| Analysis for $C_{26}H_{27}N_3O_8$ | | | |
|---|---|---|---|
| | % C | % H | % N |
| Calculated | 61.29 | 5.34 | 8.25 |
| Found | 61.28 | 5.34 | 8.24 |

IR spectrum (KBr): $\nu(cm^{-1})$: 3460, 3400, 3000, 1700, 1660, 1540, 1490, 1350, 1300, 1220, 1125, 1095, 1030, 780, 750, 700.

NMR spectrum ($\delta$, CDCl$_3$): p.p.m.: 12(1H, sd); 8.2–6.5(10H, m); 5.1(1H, s); 4.4–3.4(4H+2H, m) 2.3(6H, s); 1.2(3H, t).

EXAMPLE 31

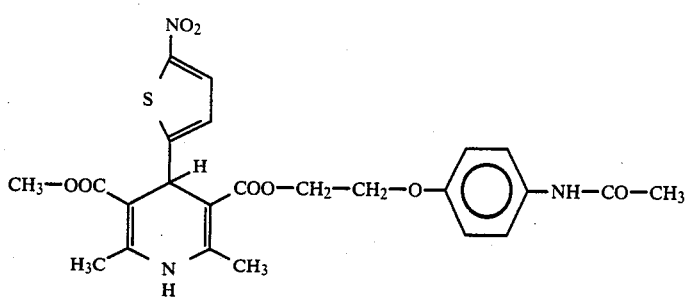

9 g (0.04 moles) of methyl 2-(5-nitro-2-thenylidene)acetylacetate and 9.81 g (0.04 moles) of 2-(4-acetylaminophenoxy)ethyl 3-aminocrotonate are heated under reflux in 40 ml of ethanol for 1.5 hours. The solution is then cooled to room temperature to obtain 2-(4-acetylaminophenoxy)ethyl 2,6-dimethyl-5-methoxycarbonyl-4-(5-nitro-2-thienyl)-1,4-dihydropyridine-3-carboxylate as yellow prismes melting and at the same time decomposing—after recrystallisation in ethanol—at 224°-226° C. The yield is 85% of the theoretical yield.

| Analysis for $C_{24}H_{25}N_3O_8S$ | | | | |
|---|---|---|---|---|
| | % C | % H | % N | % S |
| Calculated | 55.92 | 4.89 | 8.15 | 6.22 |
| Found | 55.70 | 4.70 | 8.16 | 6.54 |

IR spectrum (KBr): $\nu$(cm$^{-1}$): 3380, 3300, 3100, 1710, 1670, 1510, 1430, 1340, 1280, 1215, 1115, 1100, 1030, 840, 820, 735.

NMR spectrum ($\delta$, DMSO-d$_6$): p.p.m.: 9.7(1H, s); 9.3(1H, s); 7.9-6.7(6H, m); 5.2(1H, s); 4.5-4(2H+2H, sl+sl); 3.65(3H, s); 2.35(6H, s); 2(3H, s).

EXAMPLE 32

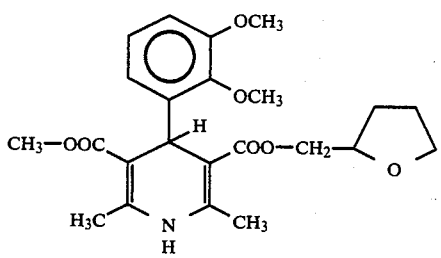

10 g (0.04 moles) of methyl 2-(2,3-dimethoxybenzylidene)acetylacetate and 7.01 g (0.04 moles) of 2-tetrahydrofurfuryl 3-aminocrotonate are heated under reflux in 40 ml of ethanol for 8 hours. The solvent is then evaporated and the remaining oil is dissolved in 10 ml of boiling ethyl acetate. The solution is cooled to −5° C. to obtain 2-tetrahydrofurfuryl 4-(2,3-dimethoxyphenyl)-2,6-dimethyl-5-methoxycarbonyl-1,4-dihydropyridine-3-carboxylate as white prisms melting—after recrystallisation in ethanol—at 138°-140° C. The yield is 48% of the theoretical yield.

| Analysis for $C_{23}H_{29}NO_7$ | | | |
|---|---|---|---|
| | % C | % H | % N |
| Calculated | 64.02 | 6.77 | 3.25 |
| Found | 63.75 | 6.75 | 3.40 |

IR spectrum (KBr): $\nu$(cm$^{-1}$): 3320, 3260, 2960, 1700, 1640, 1520, 1480, 1310, 1290, 1210, 1100, 1070, 1020, 810, 740.

NMR spectrum ($\delta$, CDCl$_3$): p.p.m.: 6.9(4H, sd); 5.3(1H, s); 4.4-3.6(5H+6H+3H, m+s+s); 2.2(6H, s); 2.1-1.7(4H, m).

EXAMPLE 33

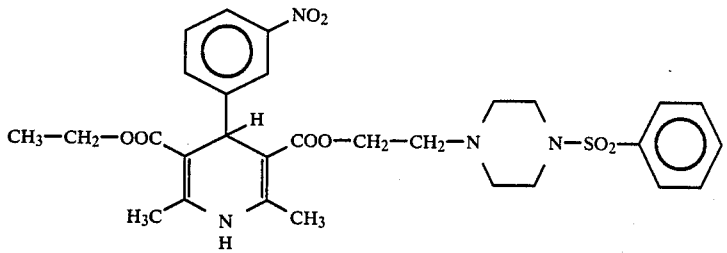

5.02 g (0.02 moles) of ethyl 2-(3-nitrobenzylidene)acetylacetate and 6.74 g (0.02 moles) of 2-(4-benzenesulfonyl-1-piperazinyl)ethyl 3-aminocrotonate are heated under reflux in 20 ml of ethanol for 8 hours. The solvent is then evaporated to obtain 2-(4-benzenesulfonyl-1-piperazinyl)ethyl 2,6-dimethyl-5-ethoxycarbonyl-4-(3-nitrophenyl)-1,4-dihydropyridine-3-carboxylate as a yellow powder melting—after recrystallisation in ethanol—at 161°-163° C. The yield is 76% of the theoretical yield.

| Analysis for $C_{29}H_{34}N_4O_8S$ | | | | |
|---|---|---|---|---|
| | % C | % H | % N | % S |
| Calculated | 58.18 | 5.72 | 9.36 | 5.36 |
| Found | 57.89 | 5.63 | 9.42 | 5.72 |

IR spectrum (KBr): $\nu$(cm$^{-1}$): 3400, 3120, 2980, 2830, 1710, 1660, 1540, 1495, 1355, 1220, 1170, 1110, 950, 740, 690.

NMR spectrum (δ, CDCl₃): p.p.m.: 8–7.1(9H, m); 6.3(1H, s); 5(1H, s); 4.2–3.8(4H, m); 3.1–2.3(10H, m); 2.3(6H, s); 1.2(3H, t).

EXAMPLE 34

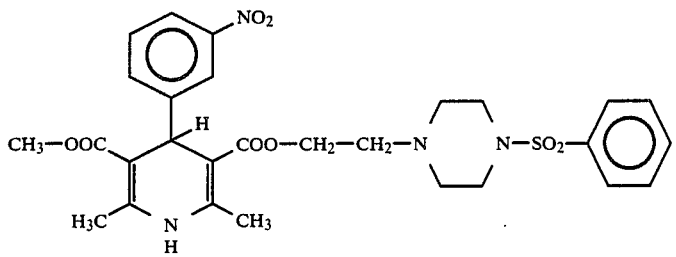

4.94 g (0.02 moles) of methyl 2-(3-nitrobenzylidene)acetylacetate and 7.0 g (0.02 moles) of 2-(4-benzenesulfonyl-1-piperazinyl)ethyl 3-aminocrotonate are heated under reflux in 20 ml of ethanol for 8 hours. The solution is then cooled to −5° C. to obtain 2-(4-benzenesulfonyl-1-piperazinyl)ethyl 2,6-dimethyl-5-methoxycarbonyl-4-(3-nitrophenyl)-1,4-dihydropyridine-3-carboxylate as yellow and slightly hygroscopic crystals melting while at the same time decomposing at—after recrystallisation in absolute alcohol—106°–120° C. The yield is 65% of the theoretical yield.

| Analysis for C₂₈H₃₂N₄O₈S | | | |
|---|---|---|---|
| | % C | % H | % N | % S |
| Calculated | 57.52 | 5.52 | 9.58 | 5.48 |
| Found | 57.45 | 5.75 | 9.62 | 5.53 |

IR spectrum (KBr): ν(cm⁻¹): 3360, 2940, 2840, 1705, 1660, 1530, 1485, 1350, 1220, 1170, 1120, 1015, 950, 740, 700, 690.

NMR spectrum (δ, CDCl₃): p.p.m.: 8.1–7.0(9H, m); 6.7(1H, s); 5(1H, s); 4.1(2H, td); 3.6(3H, s); 3.2–2.2(10H+6H, m+s).

EXAMPLE 35

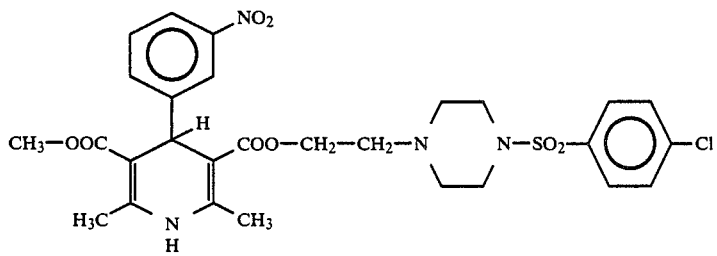

1.11 g (2.86×10⁻³ moles) of 2-(4-(4-chlorobenzenesulfonyl)-1-piperazinyl)ethyl 3-aminocrotonate and 0.72 g 2.86×10⁻³ moles) of methyl 2-(3-nitrobenzylidene)acetylacetate are heated under reflux in 10 ml of ethanol for 8 hours. The solvent is then evaporated, 3 ml of methanol are added to the residue and the mixture is cooled to −5° C. to obtain 2-(4-(4-chlorobenzenesulfonyl)-1-piperazinyl)ethyl 2,6-dimethyl-5-methoxycarbonyl-4-(3-nitrophenyl)-1,4-dihydropyridine-3-carboxylate as pale yellow cristals melting at 97°–105° C. while at the same time decomposing. The yield is 69% of the theoretical yield.

| Analysis for C₂₈H₃₁ClN₄O₈S | | | | |
|---|---|---|---|---|
| | % C | % H | % H | % Cl | % S |
| Calculated | 54.32 | 5.05 | 9.05 | 5.73 | 5.18 |
| Found | 53.97 | 5.20 | 9.26 | 5.83 | 6.32 |

IR spectrum (KBr): ν(cm⁻¹): 3360, 3080, 2940, 2810, 1700, 1530, 1480, 1350, 1210, 1170, 1090, 1010, 950, 820, 760, 700.

NMR spectrum (δ, CDCl₃): 8.1–7.2(8H, m); 6.75(1H, s) 5.1(1H, s); 4.1(2H, td); 3.6(3H, sd); 3.2–2.1(10H+6H, m+s).

EXAMPLE 36

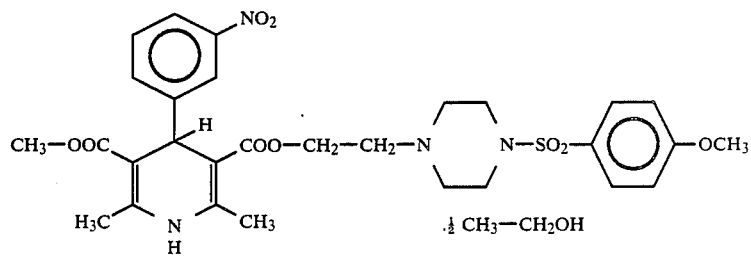

6.41 g (0.02 moles) of 2-(4-(4-methoxybenzenesulfonyl)-1-piperazinyl)ethyl 3-aminocrotonate and 4.17 g (0.02 mols) of methyl 2-(3-nitrobenzylidene)acetylacetate are heated under reflux in 20 ml of ethanol for 8 hours. The solvent is then evaporated, 5 ml of boiling methanol are added to the residue to obtain 2-(4-(4-methoxybenzenesulfonyl)-1-piperazinyl)ethyl 2,6-dimethyl-5-methoxycarbonyl-4-(3-nitrophenyl)-1,4-dihydropyridine-3-carboxylate with one half of a molecule of ethanol as yellow crystals melting while at the same time decomposing—after recrystallisation in ethanol—at 82°–104° C. The yield is 67% of the theoretical yield.

| Analysis for $C_{29}H_{34}N_4O_9S.\frac{1}{2}C_2H_6O$ | | | | |
|---|---|---|---|---|
| | % C | % N | % N | % S |
| Calculated | 56.50 | 5.85 | 8.79 | 5.03 |
| Found | 56.66 | 6.00 | 9.30 | 5.93 |

IR spectrum (KBr): $\nu(cm^{-1})$: 3360, 2940, 2830, 1700, 1590, 1530, 1500, 1350, 1220, 1160, 1090, 800, 730, 700.

NMR spectrum (δ, CDCl₃): p.p.m: 8.05–6.7(9H, m); 5.05(1H, s); 4.2–3.3(2H+3H+3H+1H, td+s+s+m); 3.1–2.2(10CH+6H, m+s); 1.2(½ 3H, t).

EXAMPLE 37

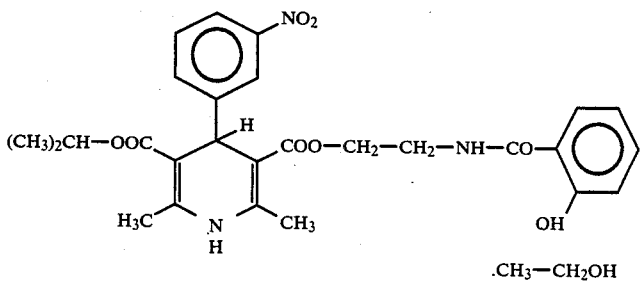

15 g (0.05 moles) of isopropyl 2-(3-nitrobenzylidene)acetylacetate and 14.30 (0.05 moles of 2-(N-salicylamido)ethyl 3-aminocrotonate are heated under reflux in 55 ml of ethanol for 8 hours. The solvent is then evaporated, 15 ml of ethyl acetate are added to the residue, and the mixture is cooled to 7° C. to obtain 2-(N-salicylamido)ethyl 2,6-dimethyl-5-isopropoxycarbonyl-4-(3-nitrophenyl)-1,4-dihydropyridine-3-carboxylate with one molecule of ethanol as yellow needles melting while at the same time decomposing at—after recrystallisation in ethanol—107°–113° C. The yield is 70% of the theoretical yield.

| Analysis for $C_{27}H_{29}N_3O_8.C_2H_6O$ | | | |
|---|---|---|---|
| | % C | % H | % N |
| Calculated | 61.15 | 6.19 | 7.38 |

| -continued | | | |
|---|---|---|---|
| Analysis for $C_{27}H_{29}N_3O_8.C_2H_6O$ | | | |
| | % C | % H | % N |
| Found | 61.45 | 6.07 | 7.62 |

IR spectrum (KBr): $\nu(cm^{-1})$: 3340, 3080, 2960, 1680, 1660, 1640, 1530, 1490, 1345, 1300, 1210, 1100, 1010, 775, 745, 695.

NMR spectrum (δ, OMSO-d₆): p.p.m.: 12.7(1H, s); 9(2H, m); 8.3–6.8(8H, m); 5.2(1H, s); 4.95(1H, m); 4.3(2H, td); 3.6(4H, m); 2.4(6H, s); 1.1(9H, t).

EXAMPLE 38

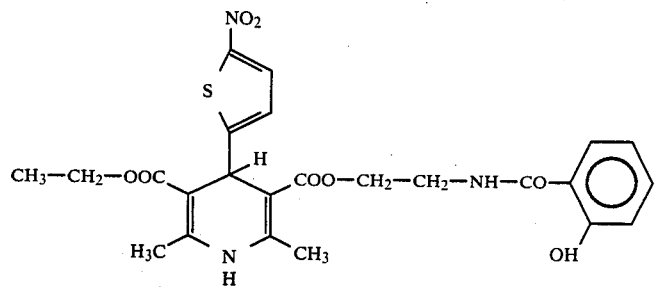

13 g (0.05 moles) of ethyl 2-(5-nitro-2-thenylidene)acetylacetate and 12.76 g (0.05 moles) of 2-(N-salicylamido)ethyl 3-aminocrotonate are heated under reflux in 100 ml of ethanol for 8 hours. The solvent is then evaporated, and the remaining oil is dried under vacuum in the presence of CaCl₂ to obtain 2-(N-salicylamido)ethyl 2,6-dimethyl-5-ethoxycarbonyl-4-(5-nitro-2-thienyl)-1,4-dihydropyridine-3-carboxylate as yellow crystals which are unstable and froth when exposed to light and which melt while decomposing at the same time at 60°–75° C. The yield is 66% of the theoretical yield.

| Analysis for $C_{24}H_{25}N_3O_8S$ | | | | |
|---|---|---|---|---|
| | % C | % H | % N | % S |
| Calculated | 55.91 | 4.89 | 8.15 | 6.22 |
| Found | 55.87 | 4.89 | 8.19 | 6.45 |

IR spectrum (KBr): $\nu(cm^{-1})$: 3360, 3100, 2980, 1700, 1650, 1600, 1500, 1335, 1210, 1120, 1090, 1020, 810, 750, 730.

NMR spectrum (δ, CDCl₃): p.p.m.: 7.6–6.6(9H, m); 5.25(1H, s); 4.5–3.5(6H, m); 2.3(6H, s); 1.2(3H, t).

EXAMPLE 39

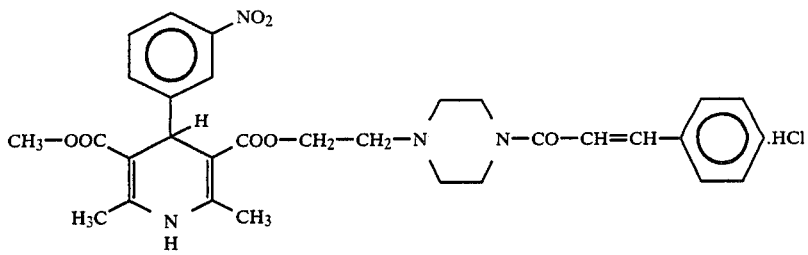

15 g (0.06 moles) of methyl 2-(3-nitrobenzylidene)acetylacetate and 20.67 g (0.06 moles) of 2-(4-cinnamoyl-1-piperazinyl)ethyl 3-aminocrotonate are heated under reflux for 8 hours in 60 ml of ethanol. The solution is then cooled to room temperature, and 1.75 ml of ethyl ether saturated with hydrogen chloride are added to obtain the chlorhydrate. The solvent is evaporated, and the residue dried under vacuum in a desiccator in the presence of $CaCl_2$ to obtain the chlorhydrate of 2-(4-cinnamoyl-1-piperazinyl)ethyl 2,6-dimethyl-5-methoxycarbonyl-4-(3-nitrophenyl)-1,4-dihydropyridine-3-carboxylate as yellow frothing crystals which melt while at the same time decomposing at 90°–150° C. The yield is 67% of the theoretical yield.

| Analysis for $C_{31}H_{34}N_4O_7.HCl$ | | | | |
|---|---|---|---|---|
|  | % C | % H | % N | % Cl |
| Calculated | 60.93 | 5.77 | 9.17 | 5.80 |
| Found | 60.73 | 5.64 | 8.82 | 5.52 |

IR spectrum (KBr): $\nu(cm^{-1})$: 3250, 3080, 2950, 1700, 1650, 1530, 1400, 1430, 1350, 1210, 1115, 1100, 1020, 760, 700.

NMR spectrum ($\delta$, $CDCl_3$): p.p.m.: 8–6.6(12H, m); 5.2(1H, s); 5(1H, s); 4.4(2H, m); 4–3.6 (4H+3H, m+s); 3(6H, m); 2,35(6H, sd).

EXAMPLE 40

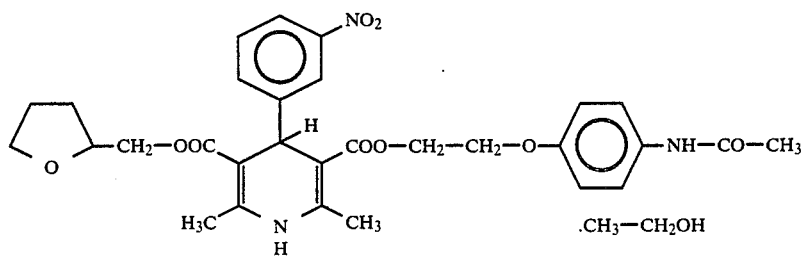

20 g (0.06 moles) of 2-tetrahydrofurfuryl 2-(3-nitrobenzylidene)acetylacetate and 17.43 g (0.06 moles) of 2-(4-acetylaminophenoxy)ethyl 3-aminocrotonate are heated under reflux in 60 ml of ethanol for 8 hours. The solvent is then evaporated, 25 ml of boiling ethyl acetate are added to the residue, and the mixture is cooled to 7° C. to obtain 2-(acetylaminophenoxy)ethyl 2,6-dimethyl-4-(3-nitrophenyl)-5-(2-tetrahydrofurfuryloxycarbonyl)-1,4-dihydropyridine-3-carboxylate with one molecule of ethanol as a yellow powder which after recrystallisation in ethyl acetate melts while at the same time decomposes at 88°–92° C. The yield is 46% of the theoretical yield.

| Analysis for $C_{30}H_{33}N_3O_9.C_2H_6O$ | | | |
|---|---|---|---|
|  | % C | % H | % N |
| Calculated | 61.43 | 6.38 | 6.72 |
| Found | 61.22 | 6.24 | 6.43 |

IR spectrum (KBr): $\nu(cm^{-1})$: 3410, 3350, 2950, 2880, 1700, 1670, 1535, 1350, 1250, 1210, 1120, 1020, 830, 750, 710.

NMR spectrum ($\delta$, $CDCl_3$): p.p.m.: 8.4–6.6(10H, m); 5.1(1H, s); 4.6–3.5(11H, s); 2.35(6H, s); 2.2–1.5(7H, m); 1.25(3H, t).

EXAMPLE 41

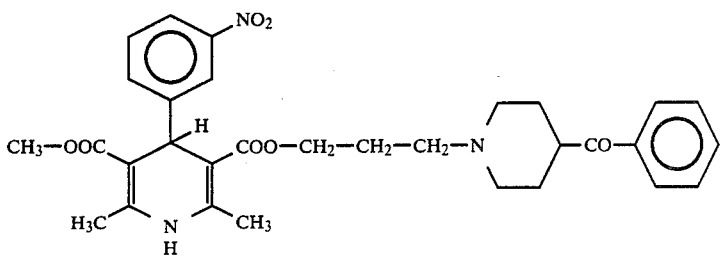

9.18 g (0.03 moles) of 3-(4-benzoyl-1-piperidinyl)propyl 3-aminocrotonate and 6.92 g (0.03 moles) of methyl 2-(3-nitrobenzenylidene)acetylacetate are heated under reflux in 30 ml of ethanol for 8 hours. The solvent is then evaporated, 10 ml of boiling methanol are added to the residue, and the mixture is cooled to −5° C. to obtain 3-(4-benzoyl-1-piperidinyl)propyl 2,6-dimethyl-5-methoxycarbonyl-4-(3-nitrophenyl-1,4-dihydropyridine-3-carboxylate as yellow crystals melting—after recrystallisation in ethanol—at 133°-136° C. The yield is 26% of the theoretical yield.

IR spectrum (KBr): $\nu(cm^{-1})$: 3360, 2940, 1700, 1650, 1530, 1510, 1350, 1210, 1115, 1090, 1020, 840, 760, 700.

NMR spectrum ($\delta$, CDCl$_3$+DMSO-d$_6$): p.p.m.: 9.4(1H, s); 8.3-6.7(10H, m); 5,05(1H, s); 4.2(2H, t); 3.6(2H+3H, m+s); 2.35(6H, s).

EXAMPLE 43

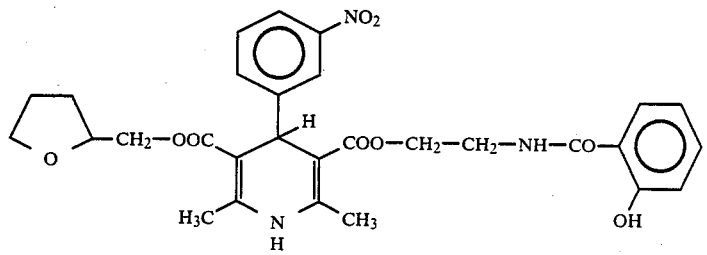

|  | Analysis for C$_{31}$H$_{35}$N$_3$C$_7$ | | |
|---|---|---|---|
|  | % C | % H | % N |
| Calculated | 66.30 | 6.28 | 7.48 |
| Found | 65.97 | 6.56 | 7.18 |

IR spectrum (KBr): $\nu(cm^{-1})$: 3380, 2960, 1705, 1680, 1660, 1530, 1485, 1350, 1220, 1120, 1100, 980, 780, 745, 700.

NMR spectrum ($\delta$, CDCl$_3$): p.p.m.: 8.1-7(10H, m); 5.1(1H, s); 4.1(2H, m); 3.6(3H, s); 3.5-1.5(5H+6H+8H).

EXAMPLE 42

15 g (0.05 moles of 2-tetrahydrofurfuryl 2-(3-nitrobenzylidene)acetylacetate and 12.41 g (0.05 moles) of 2-(N-salicylamido)ethyl 3-aminocrotonate are heated under reflux in 50 ml of ethanol for 8 hours. The solvent is then evaporated, and the remaining oil is dissolved in 30 ml of boiling aqueous ethanol (50%). The solution is then cooled to $-5°$ C. The insoluble fraction is decanted and dried under vacuum in a dessicator and in the presence of CaCl$_2$ to obtain 2-(N-salicylamido)ethyl 2,6-dimethyl-4-(3-nitrophenyl)-5-(2-tetrahydrofurfuryloxycarbonyl)-1,4-dihydropyridine-3-carboxylate as a yellow powder which after recrystallisation in ethanol melts while at the same time decomposing at 115°-125° C. The yield is 66% of the theoretical yield.

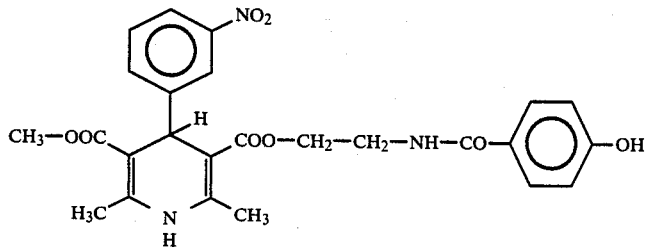

10 g (0.04 moles) of 2-(N-(4-hydroxybenzoyl)amino)ethyl 3-aminocrotonate and 9.43 g (0.04 moles) of methyl 2-(3-nitrobenzylidene)acetylacetate are heated under reflux in 40 ml of ethanol for 8 hours. The solvent is then evaporated to obtain 2-(N-(4-hydroxybenzoyl)amino)ethyl 2,6-dimethyl-5-methoxycarbonyl-4-(3-nitrophenyl)-1,4-dihydropyridine-3-carboxylate as yellow frothing crystals, which melt and at the same time decompose at 110°-120° C. The yield is 96% of the theoretical yield.

|  | Analysis for C$_{25}$H$_{25}$N$_3$O$_8$ | | |
|---|---|---|---|
|  | % C | % H | % N |
| Calculated | 60.60 | 5.08 | 8.48 |
| Found | 60.25 | 5.05 | 8.72 |

|  | Analysis for C$_{29}$H$_{31}$N$_3$O$_9$ | | |
|---|---|---|---|
|  | % C | % H | % N |
| Calculated | 61.59 | 5.52 | 7.43 |
| Found | 61.50 | 5.22 | 7.51 |

IR spectrum (KBr): $\nu(cm^{-1})$: 3440, 3360, 2960, 2860, 1700, 1650, 1530, 1490, 1340, 1220, 1120, 1015, 820, 775, 750, 690.

NMR spectrum ($\delta$, CDCl$_3$): p.p.m.: 11.9(1H, sl); 8.2-6.6(10, m); 5.1(1H, s); 4.4-3.4(9H, m); 2.35(6H, s); 2.1-1.5(4H, m).

EXAMPLE 44

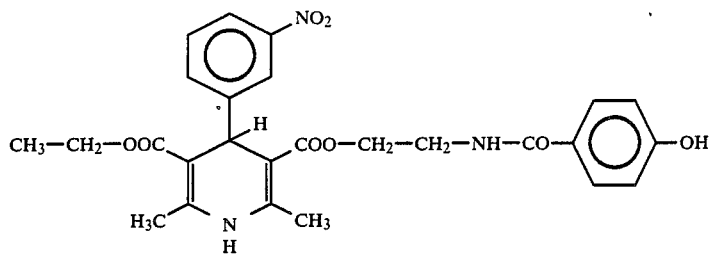

11 g (0.04 moles) of 2-(N-(4-hydroxybenzoyl)amino)ethyl 3-aminocrotonate and 10.96 g (0.04 moles) of ethyl 2-(3-nitrobenzylidene)acetylacetate are heated under reflux in 45 ml of ethanol for 8 hours. The solution is then dicoloured with activated charcoal and the solvent is evaporated to obtain 2-(N-(4-hydroxybenzoyl)amino)ethyl 2,6-dimethyl-5-ethoxycarbonyl-4-(3-nitrophenyl)-1,4-dihydropyridine-3-carboxylate as yellow frothing crystals which decompose as they melt at 107°–116° C. The yield is 72% of the theoretical yield.

| Analysis for $C_{26}H_{27}N_3O_8$ | | | |
|---|---|---|---|
| | % C | % H | % N |
| Calculated | 61.29 | 5.34 | 8.25 |
| Found | 61.98 | 5.51 | 8.25 |

IR spectrum (KBr): $\nu(cm^{-1})$: 3350, 3080, 2980, 1690, 1645, 1610, 1530, 1505, 1345, 1210, 1120, 1015, 840, 760, 740, 700.

NMR spectrum ($\delta$, $CDCl_3+DMSO-d_6$): p.p.m.: 8.4–6.6 (11H, m); 5(1H, s); 4.3–3.8(4H, m); 3.5(2H, m); 2.3(6H, s); 1.15(3H, t).

EXAMPLE 45

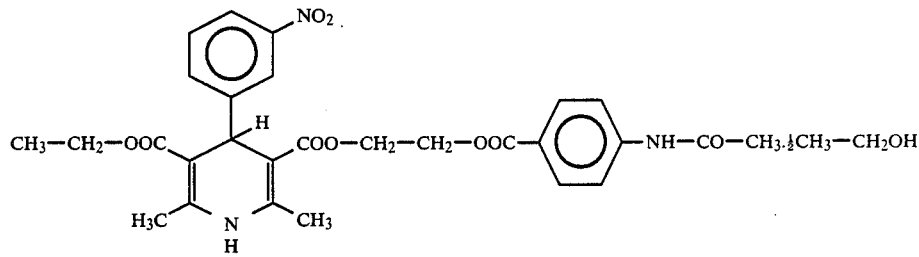

10 g (0.02 moles) of 2-(4-acetylaminobenzoyoxy)ethyl 2-(3-nitrobenzylidene)acetylacetate and 3.25 g (0.02 moles) of isopropyl 3-aminocrotonate are heated under reflux in 35 ml of ethanol for 8 hours. The solution is then cooled to −5° C. to obtain 2-(4-acetylaminobenzoyloxy)ethyl 2,6-dimethyl-5-isopropoxycarbonyl-4-(3-nitrophenyl)-1,4-dihydropyridine-3-carboxylate as yellow crystals melting—after recrystallisation in ethanol at 193°–195° C. The yield is 65% of the theoretical yield.

| Analysis for $C_{29}H_{31}N_3O_9$ | | | |
|---|---|---|---|
| | % C | % H | % N |
| Calculated | 61.59 | 5.52 | 7.43 |
| Found | 61.29 | 5.76 | 7.37 |

IR spectrum (KBr): $\nu(cm^{-1})$: 3400, 3320, 3100, 2980, 1705, 1605, 1540, 1500, 1410, 1360, 1260, 1210, 1095, 850, 769, 745, 710, 690.

NMR spectrum ($\delta$, $DMSO-d_6$): p.p.m.: 10.4(1H, s); 9.1(1H, s); 8.3–7.4(9H, m); 5.2–4.8(1H+1H, s+m); 4.45(4H, sl); 2.4 (6H, s); 2.2(3H, s); 1.15(6H, t).

EXAMPLE 46

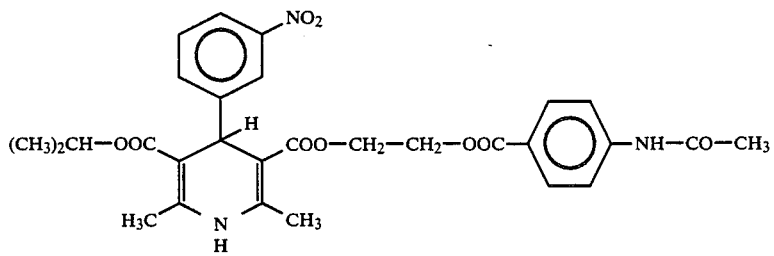

20 g (0.07 moles) of 2-(4-acetylaminobenzoyloxy)ethyl acetylacetate, 8.41 (0.07 moles) of ethyl 3-aminocrotonate and 9.84 g (0.07 moles) of 3-nitrobenzaldehyde are heated under reflux in 65 ml of ethanol for 8 hours. The solvent is then evaporated, 15 ml of boiling methanol are added to the residue, the solution is discoloured with activated charcoal and cooled to −5° C. to obtain 2-(4-acetylaminobenzoyloxy)ethyl 2,6-dimethyl-5-ethoxycarbonyl-4-(3-nitrophenyl)-1,4-dihydropyridine-3-carboxylate with half a molecule of ethanol as yellow crystals melting—after recrystallisation in ehtanol—at 157°-162° C. The yield is 46% of the theoretical yield.

| Analysis for $C_{28}H_{29}N_3O_9 \cdot \frac{1}{2}C_2H_6O$ | | | |
|---|---|---|---|
| | % C | % H | % N |
| Calculated | 60.62 | 5.61 | 7.31 |
| Found | 60.17 | 5.86 | 7.52 |

IR spectrum (KBr): $\nu(cm^{-1})$: 3360, 3250, 2990, 1720, 1690, 1660, 1630, 1475, 1345, 1270, 1210, 1110, 1090, 1050, 760, 746, 700.

NMR spectrum ($\delta$, DMSO-$d_6$): p.p.m.: 10.4(1H, s); 9.1(1H, s); 8.2-7.3(8H, m); 5.15(1H, s); 4.6-3.8(7H, m); 2.4(6H, s); 2.15(3H, s); 1.1(4, 5, t).

EXAMPLE 47

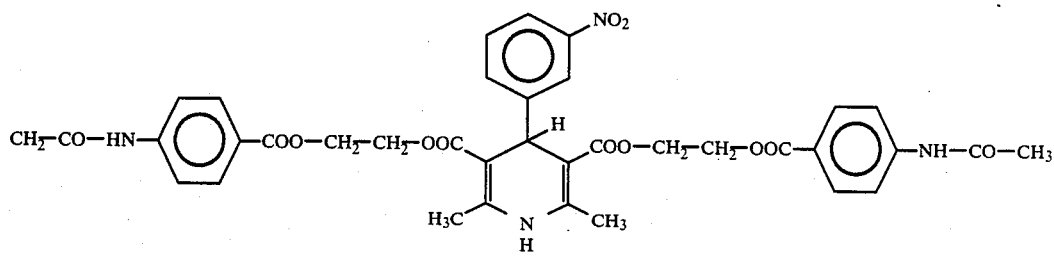

13.27 g (0.03) moles of 2-(4-acetylaminobenzoyloxy)ethyle 2-(3-nitrobenzylidene)acetylacetate, 9.26 g (0.03 moles) of 2-(4-acetylaminobenzoyloxy)ethyle acetylacetate and 5 ml of a a concentrated aqueous solution of ammonium hydroxide are heated under reflux in 50 ml of ethanol for 8 hours. 30 ml of solvent are then evaporated and the remaining fraction is cooled to $-5°$ C. to obtain bis-2-(4-acetylaminobenzoyloxy)ethyl 2,6-dimethyl-4-(3-nitrophenyl)-1,4-dihydropyridine-3,5-dicarboxylate as yellow crystals melting—after recrystallisation in ethanol—at 147°-150° C. The yield is 46% of the theoretical yield.

| Analysis for $C_{37}H_{36}O_{12}$ | | | |
|---|---|---|---|
| | % C | % H | % N |
| Calculated | 60.99 | 4.98 | 7.69 |
| Found | 60.61 | 5.15 | 7.91 |

IR spectrum (KBr): $\nu(cm^{-1})$: 3320, 3100, 2940, 1720, 1700, 1680, 1600, 1540, 1490, 1410, 1350, 1270, 1200, 1100, 850, 760, 710.

NMR spectrum ($\delta$, CDCl$_3$+DMSO-$d_6$): p.p.m.: 9.9(2H, s); 8.7(1H, s); 8.2-7(12H, m); 5(1H, s); 4.3(8H, s); 2.3(6H, s); 2.1(6H, s).

EXAMPLE 48

15 g (0.04 moles) of 2-(N-salicylamido)ethyl 2-(3-nitrobenzylidene)acetylacetate and 9.95 g (0.04 moles) of 2-(N-salicylamido)ethyl 3-aminocrotonate are heated under reflux in 40 ml of ethanol for 8 hours. The solvent is then evaporated and the remaining oil dissolved in 200 ml of methanol. The solution is discoloured with activated charcoal. The solvent is evaporated to obtain bis-2-(N-salicylamido)ethyl 2,6-dimethyl-4-(3-nitrophenyl)-1,4-dihydropyridine-3,5-dicarboxylate with one molecule of ethanol as yellow frothing crystals which melt at 107°-120° C. while at the same time decomposing. The yield is 74% of the theoretical yield.

| Analysis for $C_{33}H_{32}N_4O_{10} \cdot C_2H_6O$ | | | |
|---|---|---|---|
| | % C | % H | % N |
| Calculated | 60.86 | 5.55 | 8.11 |
| Found | 60.46 | 5.42 | 8.33 |

IR spectrum (KBr): $\nu(cm^{-1})$: 3400, 1700, 1640, 1600, 1530, 1350, 1490, 1300, 1210, 1110, 745, 690.

NMR spectrum ($\delta$, CDCl$_3$): p.p.m.: 8-6.5(18H, s); 5.05(1H, s); 4.2(4H, m); 3.8-3.4(6H, m); 2.25(6H, s); 1.2(3H, t).

EXAMPLE 49

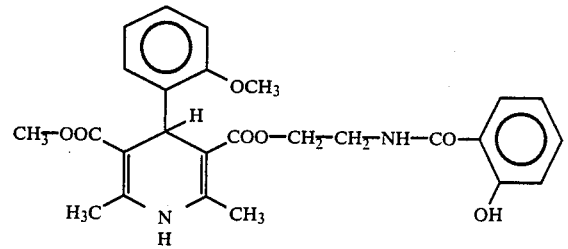

15 g (0.06 moles) of 2-(N-salicylamido)ethyl 3-aminocrotonate and 13.30 g (0.06 moles) of methyl 2-(2-methoxybenzylidene)acetylacetate are heated under reflux in 60 ml of ethanol for 8 hours. 30 ml of the solvent are then evaporated, and the remaining fraction is

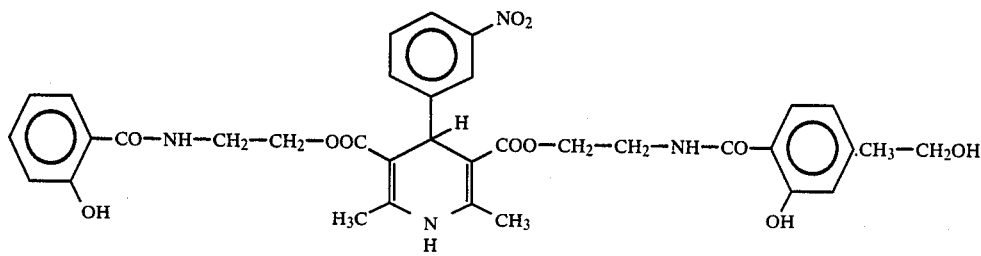

cooled to −5° C. to obtain 2-(N-salicylamido)ethyl 2,6-dimethyl-5-methoxycarbonyl-4-(2-methoxyphenyl)-1,4-dihydropridine- 3-carboxylate as pale yellow crystals melting—after recrystallisation in ethanol—at 173°–175° C. The yield is 45% of the theoretical yield.

| Analysis for $C_{26}H_{28}N_2O_7$ | | | |
|---|---|---|---|
| | % C | % H | % N |
| Calculated | 64.99 | 5.87 | 5.83 |
| Found | 64.99 | 6.14 | 6.06 |

IR spectrum (KBr): $\nu(cm^{-1})$: 3340, 3360, 2940, 1710, 1640, 1600, 1490, 1300, 1240, 1210, 1110, 1090, 1010, 755.

NMR spectrum (δ, DMSO-d$_6$): p.p.m.: 8.8(2H, m); 8.1–6.7(9H, m); 5.35(1H, s); 4.2(2H, m); 3.75(3H, s); 3.6(3H, s); 2.3(6H, s).

EXAMPLE 50

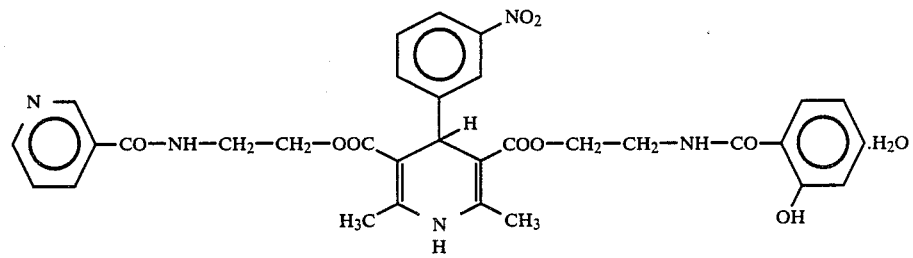

15 g (0.04 moles) of 2(N-salicylamido)ethyl 2-(3-nitrobenzylidene)acetylacetate and 9.39 g (0.04 moles) of nicotinoylamino)ethyl 3-aminocrotonate are heated under reflux in 40 ml of ethanol for 8 hours. The solution is then discoloured with activated charcoal and the solvent is evaporated. The remaining oil is recrystallised in H$_2$O$_2$, extracted with CH$_2$Cl$_2$ (2×100 ml), the ogranic phase is dried with anhydrous Na$_2$SO$_4$ and the solvent is evaporated to obtain 2-(N-salicylamido)ethyl 2-(N-nicotinoylamino)ethyl-3-carboxylate 2,6-dimethyl-4-(3-nitrophenyl)-1,4-dihydropyridine-5-carboxylate with one molecule of H$_2$O$_2$ as yellow frothing crystals which melt while at the same time decomposing at 88°–115° C. The yield is 51% of the theoretical yield.

| Analysis for $C_{32}H_{31}N_5O_9 \cdot H_2O$ | | | |
|---|---|---|---|
| | % C | % H | % N |
| Calculated | 59.35 | 5.10 | 10.82 |
| Found | 59.23 | 4.75 | 10.85 |

IR spectrum (KBr): $\nu(cm^{-1})$: 3320, 3060, 2940, 1640, 1600, 1530, 1490, 1350, 1310, 1210, 1120, 1020, 890, 750, 700.

NMR spectrum (δ, DMSO-d$_6$): p.p.m.: 12.2(1H, s); 8.9–6.7(14H, m); 5(1H, s); 4.1(4H, td); 3.5(4H, m); 3.3(2H, s); 2.25(6H, s).

EXAMPLE 51

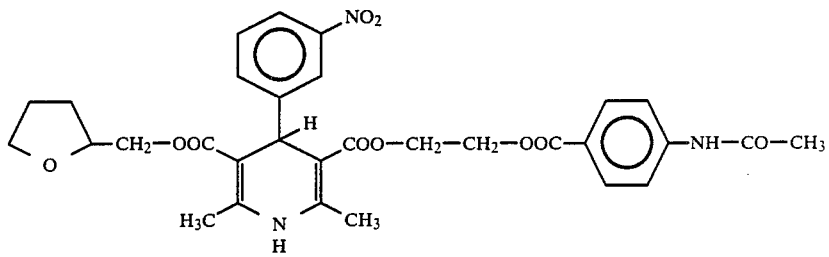

13.27 g (0.03 moles) of 2-(4-acetylaminobenzoyloxy)ethyl 2-(3-nitrobenzylidene)acetylacetate and 5.58 g (0.03 moles) of 2-tetrahydrofurfuryl 3-aminocrotonate are heated under reflux in 50 ml of ethanol for 8 hours. The solution is then discoloure with activated charcoal and the solvent evaporated to obtain 2-(4-acetylaminobenzoyloxy)ethyl 2,6-dimethyl-4-(3-nitrophenyl)-5-(2-tetrahydrofurfuryloxycarbonyl)-1,4-dihydropyridine-3-carboxylate as yellow frothing crystals which melt at 82°–92° C. while at the same time decomposing. The yield is 45% of the theoretical yield.

| Analysis for $C_{31}H_{33}N_3O_{10}$ | | | |
|---|---|---|---|
| | % C | % H | % N |
| Calculated | 61.28 | 5.47 | 6.92 |
| Found | 58.69 | 5.35 | 6.83 |

IR spectrum (KbR): $\nu(cm^{-1})$: 3350, 2950, 2880, 1700, 1600, 1530, 1490, 1350, 1270, 1210, 1090, 1010, 855, 760, 700.

NMR spectrum (δ, CDCl$_3$): p.p.m.: 8.2–7(9H, m); 6.5(1H, s); 5.1(1H, s); 4.4(4H, s); 4.1–3.6(3H+2H, s+m); 2.35(6H, s); 2.2(3H, s).

EXAMPLE 52

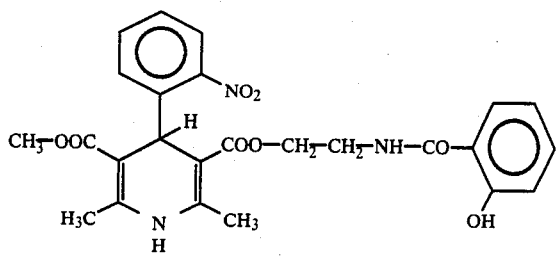

15 g (0.06 moles) of 2-(N-salicylamido)ethyl 3-aminocrotonate and 14.15 g (0.06 moles) of methyl 2-(2-nitrobenzylidene)acetylacetate are heated under reflux in 60 ml of ethanol for 8 hours. The solvent is then evaporated, 15 ml of boiling methanol are added and the mixture is cooled to −5° C. to obtain 2-(N-salicylamido)ethyl 2,6-dimethyl-5-methoxycarbonyl-4-(2-nitrophenyl)-1,4-dihydropyridine-3-carboxylate as yellow crystals melting—after recrystallisation in ethanol—at 96°–101° C. The yield is 77% of the theoretical yield.

| Analysis for $C_{25}H_{25}N_3O_8$ | | | |
|---|---|---|---|
| | % C | % H | % N |
| Calculated | 60.60 | 5.09 | 8.48 |
| Found | 60.20 | 4.94 | 8.45 |

IR analysis (KBr): $\nu(cm^{-1})$: 3380, 3080, 2960, 1710, 1650, 1600, 1540, 1500, 1360, 1310, 1215, 1090, 1020, 830, 750, 710.

NMR analysis (δ, CDCl$_3$): p.p.m.: 12.2(1H, s); 7.6–6.5(10H, m); 5.7(1H, s); 4.2(2H, sl); 3.55(2H+3H, m+s); 2.3(6H, d).

EXAMPLE 53

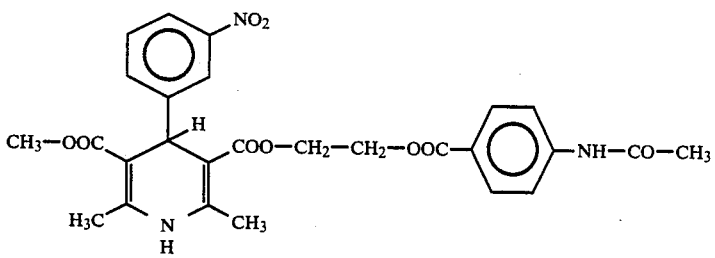

20 g (0.05 moles) of 2-(4-acetylaminobenzoyloxy)ethyl 2-(3-nitrobenzylidene)acetylacetate and 5.23 g (0.05 moles) of methyl 3-aminocrotonate are heated under reflux in 45 ml of ethanol for 8 hours. The solution is then cooled to room temperature to obtain 2-(4-acetylaminobenzoyloxy)ethyl 2,6-dimethyl-5-methoxycarbonyl-4-(3-nitrophenyl)-1,4-dihydropyridine-3-carboxylate as a yellow powder melting at 190°–193° C. The yield is 94% of the theoretical yield.

| Analysis for $C_{27}H_{27}N_3O_9$ | | | |
|---|---|---|---|
| | % C | % H | % N |
| Calculated | 60.33 | 5.06 | 7.82 |
| Found | 60.14 | 5.02 | 7.89 |

IR spectrum (KBr): $\nu(cm^{-1})$: 3360, 3240, 3100, 2960, 1720, 1700, 1660, 1530, 1480, 1350, 1270, 1210, 1110, 1090, 1000, 760, 700, 670.

NMR spectrum (δ, DMSO-d$_6$): p.p.m.: 10.1(1H, s); 8.9(1H, s); 8–7.2(8H, m); 5(1H, s); 4.4(4H, sl); 3.5(3H, s); 2.35(6H, s); 2.1(3H, s).

EXAMPLE 54

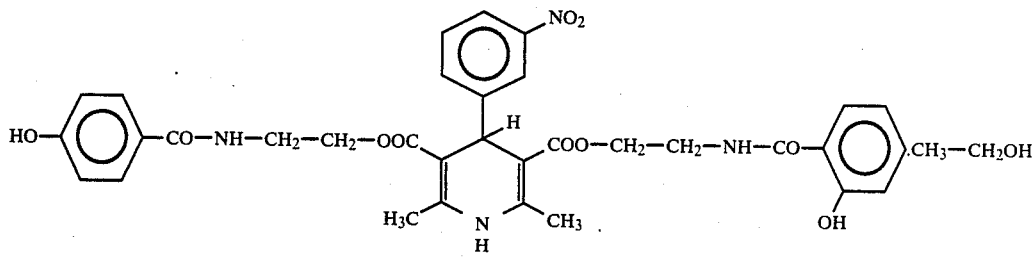

15 g (0.04 moles) of 2-(N-salicylamido)ethyl 2-(3-nitrobenzylidene)acetylacetate and 9.95 g (0.04 moles) of 2-(N-(4-hydroxybenzoyl)amino)ethyl 3-aminocrotonate are heated under reflux in ethanol for 8 hours. The solution is then discoloured with activated charcoal, and the solvent evaporated to obtain 2-(N-salicylamido)ethyl 2-(N-(4-hydroxybenzoyl)amino)ethyl-3-carboxylate 2,6-dimethyl-4-(3-nitrophenyl)-1,4-dihydropyridine-5-carboxylate with one molecule of ethanol as yellow frothing crystals which melt and decompose at the same time at 75°–100° C. The yield is 78% of the theoretical yield.

| Analysis for $C_{33}H_{32}N_4O_{10}.C_2H_6O$ | | | |
|---|---|---|---|
| | % C | % H | % N |
| Calculated | 60.86 | 5.55 | 8.11 |
| Found | 60.55 | 5.26 | 7.95 |

IR spectrum (KBr): $\nu(cm^{-1})$: 3360, 2960, 1700, 1650, 1495, 1350, 1210, 1120, 1040, 840, 750, 700.

NMR spectrum (δ, DMSO-d$_6$): p.p.m.: 8.2–6.6(17H, m); 5(1H, s); 4.15(4H, sl); 3.7–3.3(6H, m); 2.3(6H, s); 1.1(3H, t).

EXAMPLE 55

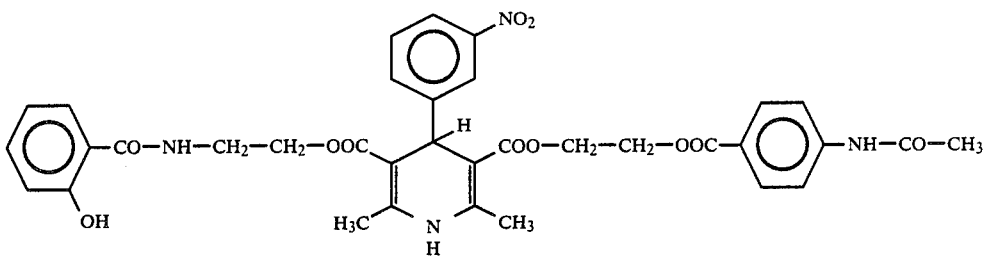

10 g (0.03 moles) of 2-(4-acetylaminobenzoyloxy)ethyl 2-(3-nitrobenzylidene)acetylacetate and 9 g (0.03 moles) of 2-(N-salicylamido)ethyl 3-aminocrotonate are heated under reflux in 40 ml of ethanol for 12 hours. 20 ml of the solvent are then evaporated and the remaining fraction is cooled to −5° C. to obtain 2-(4-acetylaminobenzoyloxy)ethyl 2-(N-salicylamido)ethyl-3-carboxylate 2,6-dimethyl-4-(3-nitrophenyl)-1,4-dihydropyridine-5-carboxylate as yellow crystals melting—after recrystallisation in aqueous 70% ethanol—at 184°–186° C. The yield is 85% of the theoretical yield.

| Analysis for $C_{35}H_{34}N_4O_{11}$ | | | |
|---|---|---|---|
| | % C | % H | % N |
| Calculated | 61.22 | 4.99 | 8.16 |
| Found | 61.11 | 5.08 | 8.01 |

IR spectrum (KBr): $\nu(cm^{-1})$: 3400, 2960, 1710, 1690, 1600, 1530, 1490, 1350, 1270, 1200, 1120, 1090, 860, 770, 740, 700.

NMR spectrum (δ, DMSO-d$_6$): p.p.m.: 12.3(1H, sl); 10.1(1H, s); 9–8.7(2H, m); 8.1–6.8(12H, m); 5.05(1H, s); 4.35(6H, m); 3.55(2H, sl); 2.35(6H, s); 2.15(3H, s).

EXAMPLE 56

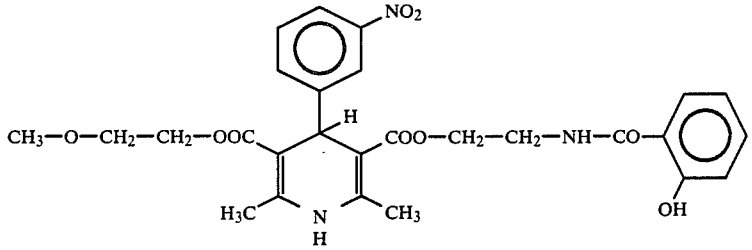

15 g (0.04 moles) of 2-(N-salicylamido)ethyl 2-(3-nitrobenzylidene)acetylacetate and 5.99 g (0.04 moles) of 2-methoxyethyl 3-aminocrotonate are heated under reflux in 40 ml of ethanol for 10 hours. The solution is then discoloured with activated charcoal, the solvent evaporated and the remaining oil dried under vacuum in a desiccator in the presence of CaCl$_2$ to obtain 2-(N-salicylamido)ethyl 2,6-dimethyl-5-(2-methoxyethoxycarbonyl)-4-(3-nitrophenyl)-1,4-dihydropyridine-3-carboxylate as frothing yellow crystals, which melt at 69°–80° C. The yield is 70% of the theoretical yield.

| Analysis for $C_{27}H_{29}N_3O_9$ | | | |
|---|---|---|---|
| | % C | % H | % N |
| Calculated | 60.11 | 5.42 | 7.79 |
| Found | 60.30 | 5.22 | 7.58 |

IR spectrum (KBr): $\nu(cm^{-1})$: 3370, 3100, 2950, 1700, 1650, 1530, 1490, 1350, 1210, 1115, 1090, 1020, 780, 750, 700.

NMR spectrum (δ, CDCl$_3$): p.p.m.: 8.1–6.5(11H, m); 5.1(1H, s); 4.2(4H, td); 3.6(4H, td); 3.3(3H, s); 2.35(6H, s).

What is claimed is:

1. A compound selected from the group consisting of esters of 1,4-dihydropyridine having the following formula

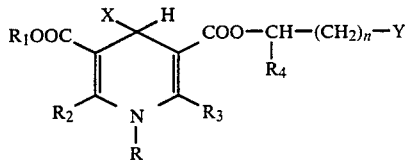

in which:

R is hydrogen or, a saturated or an unsaturated hydrocarbon radical; R$_2$ and R$_3$, which can be identical or different, are hydrogen or a straight chain alkyl group; R$_4$ is hydrogen or a straight alkyl chain;

n is a number equaling 0, 1, 2 or 3;

X is a phenyl radical which can have one to three substituents independently selected from the group consisting of nitro, cyano, azido, alkoxy, alkyl, hydroxy, alkanoyloxy, carbalkoxy, amino, alkanoyl, alkylamino, S(O)$_m$-alkyl where m equals 0, 1 or 2, phenyl, trifluoromethyl or halo;

R$_1$ is a straight or branched, saturated, unsaturated or cyclic hydrocarbon radical which can be interrupted by one or two atoms of oxygen or sulfur and which can be substituted by one or two hydroxyl groups;

$R_1$ can also designate the

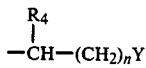

group;
where Y is a N-substituted amide of nicotinic, salicylic or hydroxybenzoic acid or a monoalkylated, monoacylated or sulfonated N-substituted piperazine of the formula

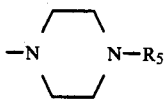

where $R_5$ is an acetyl, 2-furoyl, 2-thiophenecarbonyl, cinnamoyl or an arylsulfonyl radical; or Y is a N-(4-benzoyl-piperidinyl) group; and salts thereof.

2. A compound according to claim 1 in which:
R is hydrogen,
$R_2$ and $R_3$ are methyl,
$R_4$ is hydrogen,
X is a phenyl group with one or two substituents independently selected from the group consisting of nitro and methoxy,
n is a number equaling 0, 1 or 2,
$R_1$ is a $C_1$ to $C_4$ alkyl group, an alkoxyalkyl group with 1 or 2 carbon atoms in the alkyl portion and 1 to 3 carbon atoms in the alkoxy portion, an alkylthioalkyl group with 1 to 3 carbon atoms in the alkyl portion and in the thioalkyl portion, 3,3,5-trimethylcyclohexyl or allyl, and Y is an N-substituted amide of nicotinic, salicylic or hydroxybenzoic acid.

3. A compound according to claim 1 selected from the group consisting of 2-(N-nicotinoylamino)ethyl 2,6-dimethyl-5-methoxycarbonyl-4-(3-nitrophenyl)-1,4-dihydropyridine; 2-(N-nicotinoylamino)ethyl 2,6-dimethyl-5-ethoxycarbonyl-4-(3-nitrophenyl)-1,4-dihydropyridine-3-carboxylate; 2-(N-nicotinoylamino)ethyl 2,6-dimethyl-5-(2-methylthioethoxycarbonyl)-4-(3-nitrophenyl)-1,4-dihydropyridine-3-carboxylate; 2-(N-salicylamido)ethyl 2,6-dimethyl-5-methoxycarbonyl-5-(3-nitrophenyl)-1,4-dihydropyridine-3-carboxylate; 2-(4-(2-furoyl)-1-piperazinyl)ethyl 2,6-dimethyl-5-methoxycarbonyl)-4-(3-nitrophenyl)-1,4-dihydropyridine-3-carboxylate; 2-(4-(2-furoyl)-1-piperazinyl)ethyl 2,6-dimethyl-5-ethoxycarbonyl-4-(3-nitrophenyl)-1,4-dihydropyridine-3-carboxylate; 2-(N-salicylamido)ethyl 2,6-dimethyl-5-methoxycarbonyl-5-(3-nitrophenyl)-1,4-dihydropyridine-3-carboxylate; 2-(4-(2-furoyl)-1-piperazinyl)ethyl 2,6-dimethyl-5-methoxycarbonyl)-4-(3-nitrophenyl)-1,4-dihydropyridine-3-carboxylate; 2-(4-(2-furoyl)-1-piperazinyl)ethyl 2,6-dimethyl-5-ethoxycarbonyl-4-(3-nitrophenyl)-1,4-dihydropyridine-3-carboxylate; 2-(4-cinnamoyl-1-piperazinyl)ethyl 2,6-dimethyl-5-ethoxycarbonyl-4-(3-nitrophenyl)-1,4-dihydropyridine-3-carboxylate; 2-(N-salicylamido)ethyl 5-(2-(4-acetylaminophenoxy)ethoxycarbonyl)-2,6-dimethyl-4-(3-nitrophenyl)-1,4-dihydropyridine-3-carboxylate; 2-(N-salicylamido)ethyl 2,6-dimethyl-5-ethoxycarbonyl-4-(3-nitrophenyl)-1,4-dihydropyridine-4-carboxylate; 2-(4-benzenesulfonyl-1-piperazinyl)ethyl 2,6-dimethyl-5-ethoxycarbonyl-4-(3-nitrophenyl)-1,4-dihydropyridine-3-carboxylate; 2-(4-benzenesulfonyl-1-piperazinyl)ethyl 2,6-dimethyl-5-methoxycarbonyl-4-(3-nitrophenyl)-1,4-dihydropyridine-3-carboxylate; 2-(4-(4-chlorobenzenesulfonyl)-1-piperazinyl)ethyl 2,6-dimethyl-5-methoxycarbonyl-4-(3-nitrophenyl)-1,4-dihydropyridine-3-carboxylate; 2-(4-(4-chlorobenzenesulfonyl)-1-piperazinyl)ethyl 2,6-dimethyl-5-methoxycarbonyl-4-(3-nitrophenyl)-1,4-dihydropyridine-3-carboxylate; 2-(4-(4-methoxybenzenesulfonyl)-piperazinyl)ethyl 2,6-dimethyl-5-methoxycarbonyl-4-(3-nitrophenyl)-1,4-dihydropyridine-3-carboxylate; 2-(N-salicylamido)ethyl 2,6-dimethyl-5-isopropoxycarbonyl-5-(3-nitrophenyl)-1,4-dihydropyridine-3-carboxylate; 2-(N-salicylamido)ethyl 2,6-dimethyl-5-ethoxycarbonyl-5-(5-nitro-2-thienyl)-1,4-dihydropyridine-3-carboxylate; 2-(4-cinnamoyl-1-piperazinyl)ethyl 2,6-dimethyl-5-methoxycarbonyl-4-(3-nitrophenyl)-1,4-dihydropyridine-3-carboxylate; 2-(4-acetylaminophenoxy)ethyl 2,6-dimethyl-4-(3-nitrophenyl-5-(2-tetrahydrofurfuryoxycarbonyl)-1,4-dihydropyridine-3-carboxylate; 3-(4-benzoyl-1-piperidinyl)propyl 2,6-dimethyl-5-methoxycarbonyl-4-(3-nitrophenyl)-1,4-dihydropyridine-3-carboxylate; 2-(N-(4-hydroxybenzoyl)amino)ethyl 2,6-dimethyl-5-methoxycarbonyl-4-(3-nitrophenyl)-1,4-dihydropyridine-3-carboxylate; 2-(N-salicylamido)ethyl 2,6-dimethyl-4-(3-nitrophenyl)-5-(2-tetrahydrofurfuryloxycarbonyl)-1,4-dihydropyridine-3-carboxylate; 2-(N-(4-hydroxybenzoyl)amino)ethyl 2,6-dimethyl-5-ethoxycarbonyl-4-(3-nitrophenyl)-1,4-dihydropyridine-3-carboxylate. 2-(N-(4-hydroxybenzoyl)amino)ethyl 2,6-dimethyl-5-ethoxycarbonyl-4-(3-nitrophenyl)-1,4-dihydropyridine-3-carboxylate; bis-2-(N-salicylamido)ethyl 2,6-dimethyl-4-(3-nitrophenyl)-1,4-dihydropyridine-3,5-dicarboxylate; 2-(N-salicylamido)ethyl 2,6-dimethyl-5-methoxycarbonyl-4-(2-methoxyphenyl)-1,4-dihydropyridine-3-carboxylate; 2-(N-salicylamido)ethyl 2,6-dimethyl-4-(3-nitrophenyl)-1,4-dihydropyridine-3-carboxylate; 2-(N-salicylamido)ethyl 2,6-dimethyl-5-methoxycarbonyl-4-(2-nitrophenyl)-1,4-dihydropyridine-3-carboxylate; 2-(N-salicylamido)ethyl 2-(N-(4-hydroxybenzoyl)amino)ethyl-3-carboxylate-2,6-dimethyl-4-(3-nitrophenyl-1,4-dihydropyridine-5-carboxylate; 2-(4-acetylaminobenzoyloxy)ethyl 2-(N-salicylamido)ethyl-3-carboxylate 2,6-dimethyl-4-(3-nitropohenyl)-1,4-dihydropyridine-5-carboxylate; and 2-(N-salicylamido)ethyl 2,6-dimethyl-5-(2-methoxycarbonyl)-4-(3-nitrophenyl)-1,4-dihydropyridine-3-carboxylate.

4. A pharmaceutical composition for the treatment of atheroma, which comprises at least one ester of dihydropyridine according to claim 1, in an amount effective to exert an anti-atheromatic effect, together with a pharmaceutically acceptable diluent or carrier.

5. A pharmaceutical composition according to claim 4, containing 5–500 mg of at least one of said esters of dihydropyridine.

* * * * *